United States Patent [19]
Unger et al.

[11] Patent Number: 6,033,646
[45] Date of Patent: Mar. 7, 2000

[54] METHOD OF PREPARING FLUORINATED GAS MICROSPHERES

[75] Inventors: Evan C. Unger; Thomas A. Fritz; Terry Matsunaga; VaradaRajan Ramaswami; David Yellowhair; Guanli Wu, all of Tucson, Ariz.

[73] Assignee: ImaRx Pharmaceutical Corp., Tucson, Ariz.

[21] Appl. No.: 09/026,326

[22] Filed: Feb. 19, 1998

Related U.S. Application Data

[60] Division of application No. 08/643,070, Apr. 30, 1996, Pat. No. 5,776,429, which is a continuation-in-part of application No. 08/401,974, Mar. 9, 1995, Pat. No. 5,922,304, which is a continuation-in-part of application No. 08/159,687, Nov. 30, 1993, Pat. No. 5,585,112, which is a continuation-in-part of application No. 08/076,239, Jun. 11, 1993, Pat. No. 5,469,854, which is a continuation-in-part of application No. 08/018,112, Feb. 17, 1993, abandoned, which is a division of application No. 07/967,974, Oct. 27, 1992, Pat. No. 5,352,435, which is a division of application No. 07/818,069, Jan. 8, 1992, Pat. No. 5,230,882, which is a division of application No. 07/750,877, Aug. 26, 1991, Pat. No. 5,123,414, which is a division of application No. 07/569,828, Aug. 20, 1990, Pat. No. 5,088,499, which is a continuation-in-part of application No. 07/455,707, Dec. 22, 1989, abandoned.

[51] Int. Cl.⁷ .............................. A61K 49/04; B01J 13/02
[52] U.S. Cl. ............................. 424/9.52; 424/9.51; 264/4; 264/4.1; 427/213.3
[58] Field of Search .................................. 424/9.52, 9.51, 424/9.5, 450; 264/4, 4.1; 427/213.3

[56] References Cited

U.S. PATENT DOCUMENTS

| | | | |
|---|---|---|---|
| 3,015,128 | 1/1962 | Sommerville et al. | 18/2.6 |
| 3,291,843 | 12/1966 | Fritz et al. | 260/614 |

(List continued on next page.)

FOREIGN PATENT DOCUMENTS

| | | |
|---|---|---|
| 641363 | 3/1990 | Australia . |
| B-30351/89 | 3/1993 | Australia . |
| 0 052 575 | 5/1982 | European Pat. Off. . |
| 0 107 559 | 5/1984 | European Pat. Off. . |
| 0 077 752 B1 | 3/1986 | European Pat. Off. . |
| 0 243 947 | 4/1987 | European Pat. Off. . |
| 0 231 091 | 8/1987 | European Pat. Off. . |
| 0 272 091 | 6/1988 | European Pat. Off. . |
| 0 320 433 A2 | 12/1988 | European Pat. Off. . |
| 0 324 938 | 7/1989 | European Pat. Off. . |
| 0 338 971 | 10/1989 | European Pat. Off. . |
| 357163 A1 | 3/1990 | European Pat. Off. . |
| 0 361 894 | 4/1990 | European Pat. Off. . |
| 0 216 730 | 1/1991 | European Pat. Off. . |
| 0 467 031 A2 | 5/1991 | European Pat. Off. . |
| 441468 A2 | 8/1991 | European Pat. Off. . |
| 0 357 164 B1 | 10/1991 | European Pat. Off. . |
| 0 458 745 A1 | 11/1991 | European Pat. Off. . |
| 0 314 764 B1 | 9/1992 | European Pat. Off. . |
| 0 554 213 A1 | 8/1993 | European Pat. Off. . |
| 0 586 875 | 3/1994 | European Pat. Off. . |
| 0 614 656 A1 | 9/1994 | European Pat. Off. . |
| 0 727 225 A2 | 8/1996 | European Pat. Off. . |
| 2 700 952 | 8/1994 | France . |
| 25 21 003 | 8/1976 | Germany . |
| 62-286534 | 12/1987 | Japan . |
| 63-60943 | 3/1988 | Japan . |
| 1044680 | 10/1966 | United Kingdom . |
| 2193095A | 2/1988 | United Kingdom . |
| WO 80/02365 | 11/1980 | WIPO . |
| WO 82/01642 | 5/1982 | WIPO . |
| WO 85/01161 | 3/1985 | WIPO . |
| WO 86/00238 | 1/1986 | WIPO . |
| WO 86/01103 | 2/1986 | WIPO . |
| WO 89/05040 | 6/1989 | WIPO . |
| WO 90/01952 | 3/1990 | WIPO . |
| WO 90/04384 | 5/1990 | WIPO . |
| WO 90/04943 | 5/1990 | WIPO . |
| WO 91/00086 | 1/1991 | WIPO . |
| WO 91/03267 | 3/1991 | WIPO . |
| WO 91/12823 | 9/1991 | WIPO . |
| WO 91/15244 | 10/1991 | WIPO . |
| WO 92/10166 | 6/1992 | WIPO . |
| WO 92/11873 | 7/1992 | WIPO . |
| WO 92/15284 | 9/1992 | WIPO . |
| WO 92/17212 | 10/1992 | WIPO . |
| WO 92/17213 | 10/1992 | WIPO . |
| WO 92/17436 | 10/1992 | WIPO . |
| WO 92/17514 | 10/1992 | WIPO . |
| WO 92/21382 | 10/1992 | WIPO . |
| WO 92/22249 | 12/1992 | WIPO . |
| WO 92/22298 | 12/1992 | WIPO . |
| WO 93/00933 | 1/1993 | WIPO . |
| WO 93/05819 | 1/1993 | WIPO . |
| WO 93/06869 | 4/1993 | WIPO . |
| WO 93/13809 | 7/1993 | WIPO . |
| WO 93/17718 | 9/1993 | WIPO . |
| WO 93/20802 | 10/1993 | WIPO . |
| WO 94/00110 | 1/1994 | WIPO . |
| WO 94/06477 | 3/1994 | WIPO . |
| WO 94/07539 | 4/1994 | WIPO . |
| WO 94/09829 | 5/1994 | WIPO . |
| WO 84/02909 | 8/1994 | WIPO . |
| WO 94/16739 | 8/1994 | WIPO . |

(List continued on next page.)

OTHER PUBLICATIONS

Lejbkowicz et al., "The response of normal and malignant cells to ultrasound in vitro", Database *BIOSIS*, No. 1993:95122245 (abstract only).

Jackson et al., "Effect of ultrasound therapy on the repair of Achilles tendon injuries in rats", *Med. Sci. Sports Exercise*, 1991, 23(2), 171–176.

(List continued on next page.)

*Primary Examiner*—Jose' G. Dees
*Assistant Examiner*—Michael G. Hartley
*Attorney, Agent, or Firm*—Woodcock Washburn Kurtz MacKiewicz & Norris, LLP

[57] ABSTRACT

Lyophilized lipid compositions, as well as methods for their preparation, are embodied by the present invention. Gas-filled microspheres prepared using the lyophilized lipid composition are particularly useful, for example, in ultrasonic imaging applications and in therapeutic drug delivery systems.

22 Claims, 3 Drawing Sheets

U.S. PATENT DOCUMENTS

| | | | |
|---|---|---|---|
| 3,293,114 | 12/1966 | Kenaga et al. | 162/168 |
| 3,479,811 | 11/1969 | Walters | 57/153 |
| 3,488,714 | 1/1970 | Walters et al. | 161/161 |
| 3,532,500 | 10/1970 | Priest et al. | 96/91 |
| 3,557,294 | 1/1971 | Dear et al. | 424/342 |
| 3,594,326 | 7/1971 | Himmel et al. | 252/316 |
| 3,615,972 | 10/1971 | Morehouse et al. | 156/79 |
| 3,650,831 | 3/1972 | Jungermann et al. | 134/27 |
| 3,732,172 | 5/1973 | Herbig et al. | 252/316 |
| 3,873,564 | 3/1975 | Schneider et al. | 270/309.6 |
| 3,945,956 | 3/1976 | Garner | 270/2.5 B |
| 3,960,583 | 6/1976 | Netting et al. | 106/122 |
| 3,968,203 | 7/1976 | Spitzer et al. | 424/47 |
| 4,027,007 | 5/1977 | Messina | 424/46 |
| 4,089,801 | 5/1978 | Schneider | 252/316 |
| 4,108,806 | 8/1978 | Cohrs et al. | 521/54 |
| 4,138,383 | 2/1979 | Rembaum et al. | 270/29.7 H |
| 4,162,282 | 7/1979 | Fulwyler et al. | 274/9 |
| 4,179,546 | 12/1979 | Garner et al. | 521/56 |
| 4,192,859 | 3/1980 | Mackaness et al. | 424/5 |
| 4,224,179 | 9/1980 | Schneider | 252/316 |
| 4,229,360 | 10/1980 | Schneider et al. | 270/403 |
| 4,265,251 | 5/1981 | Tickner | 128/660 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,342,826 | 8/1982 | Cole | 435/7 |
| 4,344,929 | 8/1982 | Bonsen et al. | 424/15 |
| 4,420,442 | 12/1983 | Sands | 274/13 |
| 4,421,562 | 12/1983 | Sands et al. | 106/75 |
| 4,427,330 | 1/1984 | Sears | 270/403 |
| 4,427,649 | 1/1984 | Dingle et al. | 424/38 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,530,360 | 7/1985 | Duarte | 128/419 F |
| 4,533,254 | 8/1985 | Cook et al. | 366/176 |
| 4,534,899 | 8/1985 | Sears | 270/403 |
| 4,540,629 | 9/1985 | Sands et al. | 428/402 |
| 4,544,545 | 10/1985 | Ryan et al. | 424/1.1 |
| 4,549,892 | 10/1985 | Baker et al. | 65/21.4 |
| 4,569,836 | 2/1986 | Gordon . | |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,663,161 | 5/1987 | Mannino et al. | 424/89 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,693,999 | 9/1987 | Axelsson et al. | 514/174 |
| 4,718,433 | 1/1988 | Feinstein | 128/660 |
| 4,728,575 | 3/1988 | Gamble | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 274/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 274/4.3 |
| 4,781,871 | 11/1988 | West, III et al. | 274/4.3 |
| 4,789,501 | 12/1988 | Day et al. | 252/645 |
| 4,790,891 | 12/1988 | Halliday et al. | 149/2 |
| 4,822,534 | 4/1989 | Lencki et al. | 274/4.3 |
| 4,830,858 | 5/1989 | Payne et al. | 424/450 |
| 4,834,964 | 5/1989 | Rosen | 424/9 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 274/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et al. | 424/427 |
| 4,900,540 | 2/1990 | Ryan et al. | 424/9 |
| 4,918,065 | 4/1990 | Stindl et al. | 514/179 |
| 4,919,895 | 4/1990 | Heldebrant et al. | 422/129 |
| 4,921,706 | 5/1990 | Roberts et al. | 424/450 |
| 4,927,623 | 5/1990 | Long, Jr. | 424/5 |
| 4,933,121 | 6/1990 | Law et al. | 264/4.3 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,984,573 | 1/1991 | Leunbach | 128/653 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 A |
| 4,996,041 | 2/1991 | Arai et al. | 424/9 |
| 5,000,960 | 3/1991 | Wallach | 424/450 |
| 5,004,611 | 4/1991 | Leigh | 424/450 |
| 5,008,050 | 4/1991 | Cullis et al. | 274/4.3 |
| 5,008,109 | 4/1991 | Tin | 424/422 |
| 5,013,556 | 5/1991 | Woodle et al. | 424/450 |
| 5,019,370 | 5/1991 | Jay et al. | 424/4 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,107,842 | 4/1992 | Levene et al. | 128/662.02 |
| 5,114,703 | 5/1992 | Wolf et al. | 424/5 |
| 5,123,414 | 6/1992 | Unger | 128/654 |
| 5,135,000 | 8/1992 | Akselrod et al. | 128/662.02 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,766 | 3/1993 | Ishihara | 424/489 |
| 5,190,982 | 3/1993 | Erbel et al. | 521/56 |
| 5,192,549 | 3/1993 | Barenolz et al. | 424/450 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,196,348 | 3/1993 | Schweighardt et al. | 436/173 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,247,935 | 9/1993 | Cline et al. | 128/653.2 |
| 5,271,928 | 12/1993 | Schneider et al. | 424/9 |
| 5,281,408 | 1/1994 | Unger | 424/4 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,315,998 | 5/1994 | Tachibana et al. | 128/660.01 |
| 5,316,771 | 5/1994 | Barenholz et al. | 424/450 |
| 5,334,381 | 8/1994 | Unger | 424/9 |
| 5,339,814 | 8/1994 | Lasker | 128/653.4 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |

| | | | |
|---|---|---|---|
| 5,354,549 | 10/1994 | Klaveness et al. | 424/3 |
| 5,358,702 | 10/1994 | Unger | 424/9 |
| 5,362,477 | 11/1994 | Moore et al. | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,469,854 | 11/1995 | Unger et al. | 128/662.02 |
| 5,470,582 | 11/1995 | Supersaxo et al. | 424/489 |
| 5,485,839 | 1/1996 | Aida et al. | 128/653.1 |
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,501,863 | 3/1996 | Rössling et al. | 424/489 |
| 5,502,094 | 3/1996 | Moore et al. | 524/145 |
| 5,505,932 | 4/1996 | Grinstaff et al. | 424/9.3 |
| 5,508,021 | 4/1996 | Grinstaff et al. | 424/9.322 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,542,935 | 8/1996 | Unger et al. | 604/190 |
| 5,545,396 | 8/1996 | Albert et al. | 424/93 |
| 5,547,656 | 8/1996 | Unger | 424/9.4 |
| 5,552,133 | 9/1996 | Lambert et al. | 424/9.52 |
| 5,552,155 | 9/1996 | Bailey et al. | 424/450 |
| 5,556,372 | 9/1996 | Talish et al. | 601/2 |
| 5,556,610 | 9/1996 | Yan et al. | 424/9.52 |
| 5,558,092 | 9/1996 | Unger et al. | 128/660.03 |
| 5,558,094 | 9/1996 | Quay | 128/662.02 |
| 5,558,853 | 9/1996 | Quay | 424/9.5 |
| 5,558,854 | 9/1996 | Quay | 424/9.52 |
| 5,558,855 | 9/1996 | Quay | 424/9.5 |
| 5,558,856 | 9/1996 | Klaveness et al. | 424/9.37 |
| 5,560,364 | 10/1996 | Porter | 128/662.02 |
| 5,562,608 | 10/1996 | Sekins et al. | 604/20 |
| 5,562,893 | 10/1996 | Lohrmann | 424/9.52 |
| 5,565,215 | 10/1996 | Gref et al. | 424/501 |
| 5,567,413 | 10/1996 | Klaveness et al. | 424/9.51 |
| 5,567,414 | 10/1996 | Schneider et al. | 424/9.52 |
| 5,567,765 | 10/1996 | Moore et al. | 524/801 |
| 5,569,448 | 10/1996 | Wong et al. | 424/9.45 |
| 5,569,449 | 10/1996 | Klaveness et al. | 424/9.51 |
| 5,571,797 | 11/1996 | Ohno et al. | 514/44 |
| 5,573,751 | 11/1996 | Quay | 424/9.52 |
| 5,578,292 | 11/1996 | Schneider et al. | 424/9.51 |
| 5,585,112 | 12/1996 | Unger et al. | 424/450 |
| 5,593,680 | 1/1997 | Bara et al. | 424/401 |
| 5,595,723 | 1/1997 | Quay | 424/9.5 |
| 5,605,673 | 2/1997 | Schutt et al. | 424/9.51 |
| 5,606,973 | 3/1997 | Lambert et al. | 128/662.02 |
| 5,612,057 | 3/1997 | Lanza et al. | 424/450 |
| 5,612,318 | 3/1997 | Weichselbaum et al. | 514/44 |
| 5,614,169 | 3/1997 | Klaveness et al. | 424/9.52 |
| 5,626,833 | 5/1997 | Schutt et al. | 424/9.52 |
| 5,639,443 | 6/1997 | Schutt et al. | 424/9.52 |
| 5,643,553 | 7/1997 | Schneider et al. | 424/9.52 |
| 5,648,095 | 7/1997 | Illum et al. | 424/489 |
| 5,672,585 | 9/1997 | Pierschbacher et al. | 514/11 |
| 5,676,928 | 10/1997 | Klaveness et al. | 424/9.32 |
| 5,679,459 | 10/1997 | Riess et al. | 428/402.2 |
| 5,686,060 | 11/1997 | Schneider et al. | 424/9.52 |
| 5,686,102 | 11/1997 | Gross et al. | 424/450 |
| 5,707,352 | 1/1998 | Sekins et al. | 604/56 |
| 5,707,606 | 1/1998 | Quay | 424/9.52 |
| 5,707,607 | 1/1998 | Quay | 424/9.52 |
| 5,711,933 | 1/1998 | Bichon et al. | 424/9.52 |
| 5,716,597 | 2/1998 | Lohrmann et al. | 424/9.5 |
| 5,732,707 | 3/1998 | Widder et al. | 128/661.08 |
| 5,733,527 | 3/1998 | Schutt | 424/9.52 |
| 5,740,807 | 4/1998 | Porter | 128/662.02 |
| 5,804,162 | 9/1998 | Kabalnov et al. | 424/9.51 |
| 5,840,023 | 11/1998 | Oraevsky et al. | 600/407 |
| 5,855,865 | 1/1999 | Lambert et al. | 424/9.52 |
| 5,858,399 | 1/1999 | Lanza et al. | 424/450 |
| B1 4,229,360 | 11/1991 | Schneider et al. | 270/403 |

FOREIGN PATENT DOCUMENTS

| | | |
|---|---|---|
| WO 94/21302 | 9/1994 | WIPO . |
| WO 94/28780 | 12/1994 | WIPO . |
| WO 94/28873 | 12/1994 | WIPO . |
| WO 95/06518 | 3/1995 | WIPO . |
| WO 95/07072 | 3/1995 | WIPO . |
| WO 95/23615 | 9/1995 | WIPO . |
| WO 95/24184 | 9/1995 | WIPO . |
| WO 96/04018 | 2/1996 | WIPO . |
| WO 96/09793 | 4/1996 | WIPO . |
| WO 96/36286 | 11/1996 | WIPO . |
| WO 96/40281 | 12/1996 | WIPO . |
| WO 98/00172 | 1/1998 | WIPO . |

OTHER PUBLICATIONS

Maxwell, "Therapeutic Ultrasound: Its Effects on the Cellular and Molecular Mechanisms of Inflammation and Repair", *Physiotherapy*, 1992, 78(6), 421–426.

Tuncay et al., "Expression of Genes Associated with Tissue Remodeling Upon Ultrasound Perturbation in the Gingival Fibroblast", *J. Dental Res.*, 1996, 75, 143, (abstract only).

Wang et al., "Low Intensity Ultrasound Treatment Increases Strength in a Rat Femoral Fracture Model", *J. Orthopaedic Res.*, 1994, 12(1), 40–47.

Yang et al., "Exposure to Low–Intensity Ultrasound Increases Aggrecan Gene Expression in a Rat Femur Fracture Model", *J. Orthopaedic Res.*, 1996, 14(5), 802–809.

Young et al., "Effect of therapeutic ultrasound on the healing of full–thickness excised skin lesions", *Ultrasonics*, 1990, 28(3), 175–180.

Young et al., "The Effect of Therapeutic Ultrasound on Angiogenesis", *Ultrasound Med. Biol.*, 1990, 16(3), 261–269.

Hynynen et al., "The Usefulness of a Contrast Agent and Gradient Recalled Acquisition in a Steady–State Imaging Sequence for Magnetic Resonance Imaging–Guided Non-invasive Ultrasound Surgery", *Investigative Radiology*, 1994, 29(10), 897–903.

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography*, 1998, 11(1), 36–46.

Regen et al., "Polymerized Phosphatidylcholine Vesicles. Synthesis and Characterization", *J. Am. Chem. Soc.*, 1982, 104(3), 191–195.

Wei et al., "Quantification of Myocardial Blood Flow with Ultrasound–Induced Destruction of Microbubbles Administered as a Constant Venous Infusion", *Circulation*, 1998, 97, 473–483.

Nomura et al., "US Contrast Enhancement of Hepatic Tumor with Helium Gas Microbubbles: A Preliminary Report", *Jpn. J. Med. Ultrasonics*, 1991, 18(5), (Japanese with English language abstract).

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry,* vol. 13, No. 3, pp. 568–574 (1974).

Thanassi, "Aminomalonic Acid: Spontaneous Decarboxylation and Reaction with 5–Deoxypryridoxal", *Biochemistry,* vol. 9, No. 3, pp. 525–532 (1970).

Stelmashok et al., *Koordinatsionnaya Khimiya,* vol. 3, No. 4, pp. 524–527 (1977) (Russian and English language versions).

Mayhew et al., "High–Pressure Continuous–Flow System for Drug Entrapment in Liposomes", *Methods in Enzymology,* vol. 149, pp. 64–77 (1987).

Mayhew et al., "Characterization of Liposome Prepared Using a Microemulsifier", *Biochimica et Biophysica Acta,* vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta,* 812: 55–65 (1985).

Mayer et al., "Vesicles of Variable Size Produced by a Rapid Extrusion Procedure", *Biochimica et Biophysica Acta,* vol. 858, pp. 161–168 (1986).

Cheng, et al., "The Production and Evaluation of Contrast–Carrying Liposomes Made with an Automatic High Pressure System", *Investigative Radiology,* vol. 22, pp. 47–55 (1987).

Jain, et al., *Introduction to Biological Membranes,* Ch. 9, pp. 192–231 (J. Wiley and Sons, N.Y. 1980).

Sigel, H., ed ., *Metal Ions in Biological Systems: Antiobiotics and Their Complexes,* vol. 19 (Marcel Dekker , N.Y. 1985).

Nayar et al., "Generation of Large Unilamellar Vesicles From Long–chain Saturated Phosphatidylcholines by Extrusion Techinque", *Biochimica et Biophysica Acta,* vol. 986, pp. 200–206 (1989).

Hope et al., "Generation of Multilamellar and Unilamellar Phospholipid Vesicles", *Chemistry and Physics of Lipids,* vol. 40, pp. 89–107 (1986).

Mattrey et al., "Perfluorochemicals as US Contrast Agents for Tumor–Imaging and Hepatosplenography: Preliminary Clinical Results", *Radiology,* vol. 163, pp. 339–343 (1987).

Mattrey et al., "Perfluoroctylbromide: A Liver/Spleen–Specific and Tumor Imaging Ultrasound Contrast Materials", *Radiology,* vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography,* vol. 114, No. 3, pp. 570–575 (1987).

Feinstein et al., "Two–Dimensional Contrast Echocardiography, I: In Vitro Development and Quantitative Analysis of Echo Contrast Agents", *JACC,* vol. 3, No. 1, pp. 14–20 (1984).

Ten Cate et al., "Two–Dimensional Contrast Echocardiography, II; Transpulmonary Studies", *JACC,* vol. 3, No. 1, pp. 21–27 (1984).

Unger et al., "Hepatic Metastases: Liposomal Gd–DTPA–enhanced MR Imaging", *Radiology,* vol. 171, pp. 81–85 (1989).

Deamer et al., "Permeability of Lipid Bilayers to Water and Ionic Solutes", *Chemistry and Physics of Lipids,* vol. 40, pp.167–188 (1986).

Gutknecht et al, "Diffusion of Carbon Dioxide Through Lipid Bilayer Membranes: Effect of Carbonic Anhydrase, Bicarbonate, and Unstirred Layers", *Chemical Abstracts,* 87:34772q (1977).

Scarpa et al., "Cation Permeability of Liposomes as a Function of the Chemical Composition of the Lipid Bilayers", *Biochimica et Biophysica Acta,* vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta,* vol. 597, pp. 193–198 (1980).

Tilcock et al., "Liposomal Gd–DTPA: Preparation and Characterization of Relaxivity", *Radiology,* vol. 171, pp. 77–80 (1989).

Mann et al., "Formation of Iron Oxide in Unilamellar Vesicles", *Journal of Colloid and Interface Science,* vol. 122, No.2, pp. 326–335 (1988).

Anderson et al., "Manganese (III) Complexes in Oxidative Decarboxylation of Acids", *J. Am. Chem. Soc.,* vol. 92, No.8, pp. 2450–2460 (1970).

Muhlradt et al., "Vitamin B6 Analogs: An Improved Synthesis of 5–Deoxypyridoxal", *New Compounds,* vol. 10, pp. 129–130 (1967).

Chapman D., "Physiochemical Properties of Phospholipids and Lipid Water Systems", *Liposome Technology,* Gregoriadis, G., ed., vol. 1, pp. 1–18 (CRC Press, Boca Raton, FL, 1984).

Violante et al., "Particulate Suspensions as Ultrasonic Contrast Agents for Liver and Spleen", *Inv. Rad.,* vol. 23, pp. S294–S297, Sep. 1988.

Fritzsch et al., "Preclinical and Clinical Results with an Ultrasonic Contrast Agent", *Inv. Rad.,* vol. 23, pp. S302–S305, Sep. 1988.

Brochure, *Experience,* Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.,* vol. 108, pp. 2321–2327 (1986).

Regen, "Polymerized Vesicles", *J. Am. Chem. Soc.,* vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC),* vol. 44(3), pp. 322–326 (1981) (abstract).

J. Vion–Dury et al., *J. Pharmacol. Exper. Ther.,* vol. 250(3), pp. 1113–1118 (1989) (abstract).

M.R. Zalutsky et al., *Invest. Radiol.,* vol. 22(2), pp. 141–147 (1987) (abstract).

Crowe et al., *Archives of Biochemistry and Biophysics,* vol. 242, pp. 240–247 (1985).

Crowe et al., *Archives of Biochemsitry and Biophysics,* vol. 220, pp. 477–484 (1983).

Dorland's Illustrated Medical Dictionary, p. 946, 27th ed. (W.B. Saunders Company, Philadelphia 1988).

*Liposome Technology,* Gregoriadis, G., ed ., vol. I, pp. 30–35, 51–65 and 79–107 (CRC Press Inc., Boca Raton, FL, 1984).

Madden et al., *Chemistry and Physics of Lipids,* vol. 53, pp. 37–46 (1990).

Sinkula et al., *J. Pharm. Sci.*, vol. 64, pp. 181–210 (1975).
Shiina et al., "Hyperthermiably Low–frequency Synthesized Ultrasound", *IEEE Engineering*, pp. 879–880, vol. 2 (1988) (abstract).
McAvoy et al., *IEEE Engineering, Ultrasonics Symposium Proceedings*, vol. 2, pp. 677–1248 (1989) (abstract).
Chapman et al., "Biomembrane Phase Transitions", *J. Biol. Chem.*, 1974, 249:2512–2521.
Hug et al., "Liposomes for the Transformation of Eukaryotic Cells", *Biochmimica et Biophysica Acta*, 1991, 1097:1–17.
Marsh, *CRC Handbook of Lipid Bilayers* (CRC Press, Boca Raton, FL 1990) pp. 139–141.
Szoka et al., "Procedure for Preparation of Liposomes With Large Internal Aqueous Space . . . ", *Proc. Natl. Acad. Sci.* 1978, 75:4194–4198.
Acoustic Imaging; AI5200; Convex Curved Linear Array Ultrasound Transducers Operator's Manual, Nov. 20, 1989, 4700–0003–1C, p. 4.
Bangham et al., "Diffusion of Univalent Ions across the Lamellae of Swollen Phospholipids", *J. Mol. Biol.*, 1965, 13:238–252.
Carson et al., *Ultrasound in Med. & Biol. 3*, 1978, 341–350.
Kost et al., *Polymers in Medicine II: Biomedical and Pharmaceutical Applications*, "Ultrasonic Modulated Drug Delivery Systems", Chiellini et al., ed., (Plenum Press, New York and London), pp. 387–396 (1985).
deGier et al., "Relations Between Liposomes and Biomembranes", *Annals of The New York Academy of Sciences*, 1978, 308:85–99.
Felgner et al.,"Lipofection: A highly efficient , lipid–mediated DNA–transfection procedure", *Proc. Natl. Acad. Sci.*, 1987, 84:7413–7417.
Gabizon et al., "Liposome formulations with prolonged circulation time in blood and enhanced uptake by tumors", *Proc. Natl. Acad. Sci.*, 1988, 85:6949–6953.
Garelli, et al., *Biochimica et Biophysica Acta*, vol. 1127:41–48 (1992).
Kawai et al., "New Procedure for DNA Transfection with Polycation and Dimethyl Sulfoxide", *Molecular and Cellular Biology*, 1984, 4:1172–1174.
Kuo et al., "Metallocene Antitumor Agents. Solution and Solid–State Molybdenocene Coordination . . . ", *J. Am. Chem. Soc.*, 1991, 113:9027–9045.
MacDonald, *Mammalian Cell Biotechnology: A Practical Approach*, M. Butler, ed., 1991 (Oxford University Press, New York), pp. 57–70.
Mathiowitz et al., "Photochemical Rupture of Microcapsules: A Model System", *Journal of Applied Polymer Science*, 1981, 27:809–822.
May et al., "Cationic Liposomes Enable Bovine Herpesvirus Type 2 DNA to Infect Cells", *Acta virol.*, 1991, 35:107.
Poznansky et al., "Biological Approaches to the Controlled Delivery of Drugs: A Critical Review", *Pharmacol, Rev.*, 1984, 36:277–336.
Sato et al., "Recent Aspects in the Use of Liposomes in Biotechnology and Medicine", *Prog. Lipid Res.* 1992, 4:345–372.
Simons et al., "Antisense c–myb oligonucleotides inhibit intimal arterial smooth muscle cell accumulation in vivo", *Nature,* 1992, 359:67–70.
Thompson, Larry, "At Age 2, Gene Therapy Enters a Growth Phase", *Science* 1992, 258:744–746.
Trubetskoy et al., "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE*, 1992, O–7803–0785, pp. 354–355.
Williams, "Human Gene Therapy: Searching for Better Vectors", *ASM News* [American Society for Microbiology] 1992, 58:67–69.
Woodle et al., "Versatility in lipid compositions showing prolonged circulation . . . ", *Biochimica et Biophysica Acta* 1992, 1105:193–200.
Zhou et al., "Targeted delivery of DNA by liposomes and polymers", *J. of Controlled Release* 1992, 19:269–274.
Mathiowitz et al., "Polyanhydride Microspheres as Drug Carriers", *Journal of Applied Polymer Science*, vol. 35, pp. 755–774 (1988).
Sankaram et al., "Cholesterol–Induced Fluid–Phase Immiscibility in Membranes", *Proc. Natl. Acad. Sci.*, vol. 88, pp. 8686–8690 (1991).
*Scientific Apparatus Catalog 92/93* (VWR Scientific, 1991), "Syringes", pp. 1511–1513; Filtration, Syringe Filters, pp. 766–768; Filtration, Membranes, pp. 750–753; Filtration, Filter Holders, p. 744.
Gramiak et al., *Radiology*, "Detection of Intracardiac Blood Flow by Pulsed Echo–Ranging", pp. 415–418 (1971).
Feigenbaum et al., *Circulation*, "Identification of Ultrasound Echoes from the Left Ventricle by Use of Intracardiac Injections of Indocyanine Green", vol. XL1, pp. 615–631 (1970).
Santaella, et al., *FEBS 13463*, "Extended In Vivo Blood Circulation Time of Fluorinated Liposomes", vol. 336, No. 3, pp. 481–484 (1993).
Brown and Lager, *Annual Review Medicine*, 1988, 39:221 29, Annual Review, Inc., "Transdermal Delivery of Drugs", pp. 221–229.
Moseley, et al., *Microbubbles: A Novel MR Susceptibility Contrast Agent*, abstract, 1991 Napa, California Meeting of the Society for Magnetic Resonance in Medicine.
Ter–Pogossian *Tomography*, Kee, et al., n, "Physical Principles and Instrumentation", *Computed Body eds.*,Raven Press, New York, Chapter 1, pp. 1–7 (1988).
Aronberg, "Techniques", *Computed Body Tomography*, Kee, et al., eds., Raven Press, New York, Chapter 2, pp. 9–36 (1988).
Miller, *Ultrasonics* (Sep. 1981), "Ultrasonic detection of resonant cavitation bubbles in a flow tube by their second-–harmonic emissions," pp. 217–224.
Dittrich, "Cardiac Muscle Ischemia and Infarction", *The Second Annual International Symposium on Contrast Agents in Diagnostic Ultrasound*, Atlantic City, NJ (May 7, 1996).
Pantely, "Intravenous Contrast Echocardiography–Tissue Imaging & Quantification of Coronary Blood Flow", *The Second Annual International Symposium on Contrast Agents in Diagnostic Ultrasound*, Atlantic City, NJ (May 7, 1996).
Schutt et al., "Osmotically Stabilized Microbubble Sonographic Contrast Agents",*Acad. Radiol.*, vol. 3, Suppl. 2, pp. S188–S190 (Aug. 1996).
Frézard, et al., "Permeability and stability in buffer and in human serum of fluorinated phospholipid–based liposomes", *Biochimica et Biophysica Acta*, 1192, pp. 61–70 (1994).
Frézard, et al., "Fluorinated Phospholipid–Based Vesicles as Potential Drug Carriers: Encapsulation/Sustaining of Drugs and Stability in Human Serum",*Art, Cells, Blood Subs., and Immob. Biotech.*, 22(4), pp. 1403–1408 (1994).
Chang et al., "Semipermeable Aqueous Microcapsules", *Canadian J. of Phys. and Pharm.*, 1966, 44, 115–128.

Chang, "Semipermeable Microcapsules", *Science,* 1964, 146, 524–525.

Deasy, *Microencapsulation and Related Drug Processes,* 1983, vol. 20, Chs. 9 and 10, 195–240 (Marcel Dekker, Inc., NY).

Yeung et al., "Preparation of Microencapsulated Liposomes", *J. Microencapsulation,* 1988, 5, 331–337.

Mattrey et al., *Gas Emulsions as Ultrasound Contrast Agents; Preliminary Results in Rabbits and Dogs, Investigative Radiology,* vol. 29, Jun. Supp. 2, pp. S139–S141, 1994.

Meltzer et al., *Transmission of Ultrasonic Contrast Through the Lungs, Ultrasound in Med. & Biol.,* vol. 7, No. 4, 377–384, 1981.

PR Newswire, Apr. 1, 1986.

Swanson et al., Chapter 22, "Enhancement Agents for Ultrasound: Fundamentals", *Pharmaceuticals In Medical Imaging,* pp. 682–687 (1990).

Ophir et al., "Contrast Agents in Diagnostic Ultrasound", *Ultrasonic in Med. & Biol.,* vol. 15, No. 4, pp. 319–333 (1989).

Jacobs, "Intraocular gas measurement using A–scan ultrasound", *Current Eye Research,* vol. 5, No. 8, pp. 575–578 (1986).

Lincoff et al., "Intravitreal Expansion of Perfluorcarbon Bubbles", *Arch. Ophthamol.,* vol. 98, p. 1646, Sep. 1980.

Lincoff et al., "Intravitreal Longevity of Three Perfluorcarbon Gases", *Arch. Ophthamol.,* vol. 98, pp. 1610–1611, Sep. 1980.

Lincoff et al., "The Perfluorcarbon Gases in the Treatment of Retinal Detachment", *Ophthamology,* vol. 90, No. 5, pp. 546–551, May 1983.

Gardner et al., "A Survey of Intraocular Gas Use in North America", *Arch. Ophthamol.,* vol. 106, pp. 1188–1189, Sep. 1988.

Unger et al., "Liposome MR Contrast Agents", *J. Liposome Research,* 4(2), pp. 811–834 (1994).

Feinstein, Steven B., "Myocardial Perfusion Imaging: Contrast Echocardiography Today and Tomorrow," *Journal of the American College of Cardiology,* 8(1):251–253 (1986).

Keller et al., "The Behavior of Sonicated Albumin: Microbubbles Within the Microcirculation: A Basis for Their Use During Myocardial Contrast Echocardiography", *Circulation Res.,* 65(2):458–465 (1989).

Lincoff et al., "Perfluoro–n–butane: A Gas for Maximum Duration Retinal Tamponade," *Arch. Ophthalmology,* 101:460–462 (1983).

*Remington's Pharmaceutical Sciences,* John Hoover, managing ed., Mack Publishing Company, Easton, PA, pp. 295–298; 736; 1242–1244 (1975).

*Handbook of Pharmaceutical Excipients,* American Pharmaceutical Association, Washington, D.C. and The Pharmaceutical Society of Great Britain, London, England, pp. 181–183 (1986).

Barnhart et al., "Characterization of Albunex™: Air–Filled Microspheres for Echocardiography Contrast Enhancement," *Investigative Radiology,* 25:S162–164 (1990).

Levene et al., "Characterization of Albunex™," *J. Acoust. Soc. Am.,* 87(Suppl.1):569–70 (1990).

Miller et al., "Physiochemical Approaches to the Mode of Action of General Anesthetics," *J. Amer. Soc. Anesthesiologists,* 36(4):339–351 (1972).

"Properties and Applications of the 'Freon' Fluorocarbons" in DuPont Freon Technical Bulleting B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Acience and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials,* 11:713–717 (1990).

Villanueva et al., "Characterization of Spatial Patters of Flow Within the Reperfused Myocardium by Myocardial Contrast Echocardiography", *Circulation,*vol. 88, No. 6, pp. 2596–2606 (Dec. 1993).

Desir et al., "Assessment of regional myocardial perfusion with myocardial contrast echocardiography in a canine model of varying degress of coronary stenosis", *American Heart Journal,* vol. 127, No. 1, pp. 56–63 (Jan. 1994).

Sekins et al., "Lung Cancer Hyperthermia via Ultrasound and PFC Liquids", *Published in Proceeding of 5th International Symposium on Hyperthermic Oncology,* Kyoto, Japan, (3 pages) (Aug. 29–Sep. 3, 1998).

Pietersen, "A New Warning System for Fires of Electrical Origin", *CERN European Organization for Nuclear Research, Health and Safety Division,* pp. 1–5 (Mar. 1977).

METHOD OF PREPARING FLUORINATED GAS MICROSPHERES

RELATED APPLICATIONS

This application is a divisional of Ser. No. 08/643,070, filed Apr. 30, 1996, U.S. Pat. No. 5,776,429, which is continuation in part of application U.S. Ser. No. 08/401,974, filed Mar. 9, 1995, U.S. Pat. No. 5,922,384, which is a continuation in part of U.S. Ser. No. 08/159,687, filed Nov. 30, 1993, U.S. Pat. No. 5,585,112, which is a continuation in part of U.S. Ser. No. 08/076,239, filed Jun. 11, 1993, now U.S. Pat. No. ,5,469,854, which is a continuation in part of U.S. Ser. No. 08/018,112, filed Feb. 17, 1993, now abandoned, which is a divisional of U.S. Ser. No. 07/967, 974, filed Oct. 27, 1992, now U.S. Pat. No. 5,352,435, which is a divisional of U.S. Ser. No. 07/818,069, filed Jan. 8, 1992, now U.S. Pat. No. 5,230,882, which is a divisional of U.S. Ser. No. 07/750,877, filed Aug. 26, 1991, now U.S. Pat. No. 5,123,414, which is a divisional of U.S. Ser. No. 07/569,828, filed Aug. 20, 1990, now U.S. Pat. No. 5,088,499, which is a continuation in part of application U.S. Ser. No. 07/455, 707, filed Dec. 22, 1989, now abandoned.

BACKGROUND OF THE INVENTION

Field of the Invention

This invention relates to the field of methods for preparing a lyophilized lipid composition and gas-filled microspheres. The lyophilized lipid composition is especially useful in the preparation of gas-filled microspheres in accordance with the methods of the present invention. Microspheres prepared by these methods are particularly suitable, for example, in ultrasonic imaging applications and in therapeutic delivery systems.

Background of the Invention

Preparations of conventional lipids and lipid blends are generally dispersed to a standard of uniformity by dispersion of the product in organic solvents such as cyclohexane:ethanol mixtures, followed by freezing and subsequent drying in vacuo (freeze drying) to yield a mixture. Conventional preparations of lipid dispersions or dry lipid blends are limited by process of making them whereby the lipids are solvated in organic solvents with dissimilar physical properties (i.e. solubility coefficients, polarity) to water or aqueous-based formulations. This presents a problem as the dispersions are very difficult to rehydrate with aqueous-based formulations. In addition, the standard of uniformity is extremely low, unlike the consistent uniformity exemplified by the ratio of the lipids of the present invention throughout the lipid composition. The time and ability to rehydrate conventional dispersions into a pharmaceutically acceptable preparation is severely limited. Oftentimes, lipid particles do not hydrate adequately and remain as undispersed, insoluble, pharmaceutically unacceptable formulations and the inability of the lipid particles to be sterile filtered through one or more 0.2 $\mu$m filters. The lipid preparations of the prior art are not sufficiently dispersed and subsequently can not be filtered from the solution when the dispersion is filtered through a 0.22 $\mu$m filter. The unfiltered moieties result in batch to batch variation of the ratio of lipids in the composition. The lipid dispersions are often processed to determine the total lipids ultimately dispersed into the formulations. This process is not acceptable because it often leads to formulations that are difficult to prepare and the resulting formulations are of unknown lipid quantity. In addition, the manufacturing process is inefficient and ineffective due to the time and cost of the process. These and/or problems have been addressed in the present invention.

BRIEF DESCRIPTION OF THE PRIOR ART

Janoff et al., in U.S. Pat. No. 4,880,635, published PCT application WO 86/01103, and published European Patent applications 0 562 641 A1 and 0 562 424 A1, disclose dehydrated liposomes prepared by drying liposome preparations under reduced pressure in the presence of one or more protective sugars, such as disaccharides. The protective sugar may be omitted if the following conditions are met: the liposomes have multiple lipid layers; the dehydration is done without prior freezing, and the dehydration is performed to an end point which results in at least 12 moles water/mole lipid being retained in the preparation to maintain the integrity of the multiple lipid layers upon rehydration.

Huang et al., in U.S. Pat. No. 4,927,571, disclose the encapsulation of doxorubicin in liposomes. The methods disclosed for liposome preparation by Huang et al. include 1) thin film hydration such that a very thin dry film of lipids are prepared by drying and 2) a solvent injection, that produces a high concentration dispersion (greater than 40 mM lipid).

Gamble, in U.S. Pat. No. 4,753,788, disclose a method for preparing small lipid vesicles by microemulsification. A lipid and cholesterol are dissolved in chloroform and dried to form a thin film. The resulting film is dried in a vacuum and rehydrated.

Schneider et al., in Reexamined U.S. Pat. No. B1 4,229, 360, disclose a process for dehydration of liposomes for storage in a powder form such that the liposomes may be used at a later date.

Hauser, in U.S. Pat. No. 5,089,181, discloses a method of dehydrating unilamellar lipid vesicles by evaporating a vesicle-containing aqueous media in the presence of a preserving additive at a temperature of 60° C. to 150° C.

Collins, in published PCT application WO 95/12387, discloses a method for encapsulating and delivering biologically active materials for drug delivery. The encapsulation method comprises one or more cycles of freezing and thawing the liposomes and dehydrating the liposome dispersion to form a lipid powder.

Accordingly, new and/or better lyophilized compositions and microspheres and methods for providing same are needed. The present invention is directed to this, as well as other, important ends.

SUMMARY OF THE INVENTION

In one embodiment, the present invention is directed to a microsphere filled with a fluorine-containing gas, comprising a blend of the lyophilized lipids dipalmitoylphosphatidylcholine (DPPC), dipalmitoylphosphatidylethanolamine-polyethylene glycol (DPPE-PEG), and dipalmitoylphosphatidic acid (DPPA) and a perfluorocarbon gas in an aqueous-based carrier. The lipids of the microsphere are preferably combined in a ratio of about 70 to about 90 mole % DPPC, about 5 to about 15 mole % DPPE-PEG, and about 5 to about 15 mole % DPPA. The combined concentration of the lipids dispersed in an aqueous-based pharmaceutically acceptable carrier is preferably about 0.1 mg/ml to about 5 mg/ml, more preferably about 3 mg/ml, even more preferably about 1 mg/ml. Polyethylene glycol (PEG) useful in the lipid composition and microspheres of the present invention may have a molecular weight of about 4,000 to about 200,000, more preferably about 1,000 to about 20,000, even more preferably about 2,000 to about 8,000, and most preferably about 5,000.

In a second embodiment, the present invention is directed to a lyophilized lipid composition. The lipid composition comprises a blend of the lipids dipalmitoylphosphatidylcholine, dipalmitoylphosphatidylethanolamine-polyethylene glycol, and dipalmitoylphosphatidic acid, in a ratio of about 70 to about 90 mole %, about 5 to about 15 mole %, about 5 to about 15 mole %, respectively. The combined concentration of lipids is preferably about 20 mg/ml to about 50 mg/ml, more preferably about 40 mg/ml, more preferably about 30 mg/ml, even more preferably about 25 mg/ml of aqueous solution prior to lyophilization.

The third embodiment of the present invention comprises a method of preparing a microsphere filled with a fluorine-containing gas comprising obtaining a lyophilized lipid composition comprising the lipids dipalmitoylphosphatidylcholine, dipalmitoylphosphatidylethanolamine-polyethylene glycol, and dipalmitoylphosphatidic acid, in a ratio of about 70 to about 90 mole percent, about 5 to about 15 mole percent, and about 5 to about 15 mole percent, respectively, wherein the combined concentration of lipids is about 20 mg/ml to about 50 mg/ml of aqueous solution prior to lyophilizing; dispersing the lyophilized composition in an aqueous-based pharmaceutically acceptable carrier to a concentration of about 0.1 mg/ml to about 5 mg/ml to form an aqueous microsphere-forming solution; introducing a fluorine-containing gas into the aqueous microsphere-forming solution to form a fluorine-containing aqueous microsphere-forming solution; and shaking the aqueous microsphere-forming solution to form a fluorine-containing gas-filled microsphere.

A fourth embodiment of the present invention is a method for preparing a lyophilized lipid composition comprising dispersing the lipids dipalmitoylphosphatidylcholine, dipalmitoylphosphatidylethanolamine-polyethylene glycol, and dipalmitoylphosphatidic acid in a ratio of about 70 to about 90 mole % DPPC, about 5 to about 15 mole % DPPE-PEG, and about 5 to about 15 mole % DPPA, in an aqueous carrier to a concentration of about 20 mg/ml to about 50 mg/ml to form a lipid-containing aqueous solution; and lyophilizing the lipid-containing aqueous solution to form a lyophilized lipid composition such that the dipalmitoylphosphatidylcholine, dipalmitoylphosphatidylethanolaminepolyethylene glycol, and dipalmitoylphosphatidic acid ratio of about 70 to about 90 mole %, about 5 to about 15 mole %, and about 5 to about 15 mole %, respectively, is uniform throughout the composition.

These and other aspects of the invention will become more apparent from the following detailed description.

DETAILED DESCRIPTION OF THE INVENTION

Figure 1:
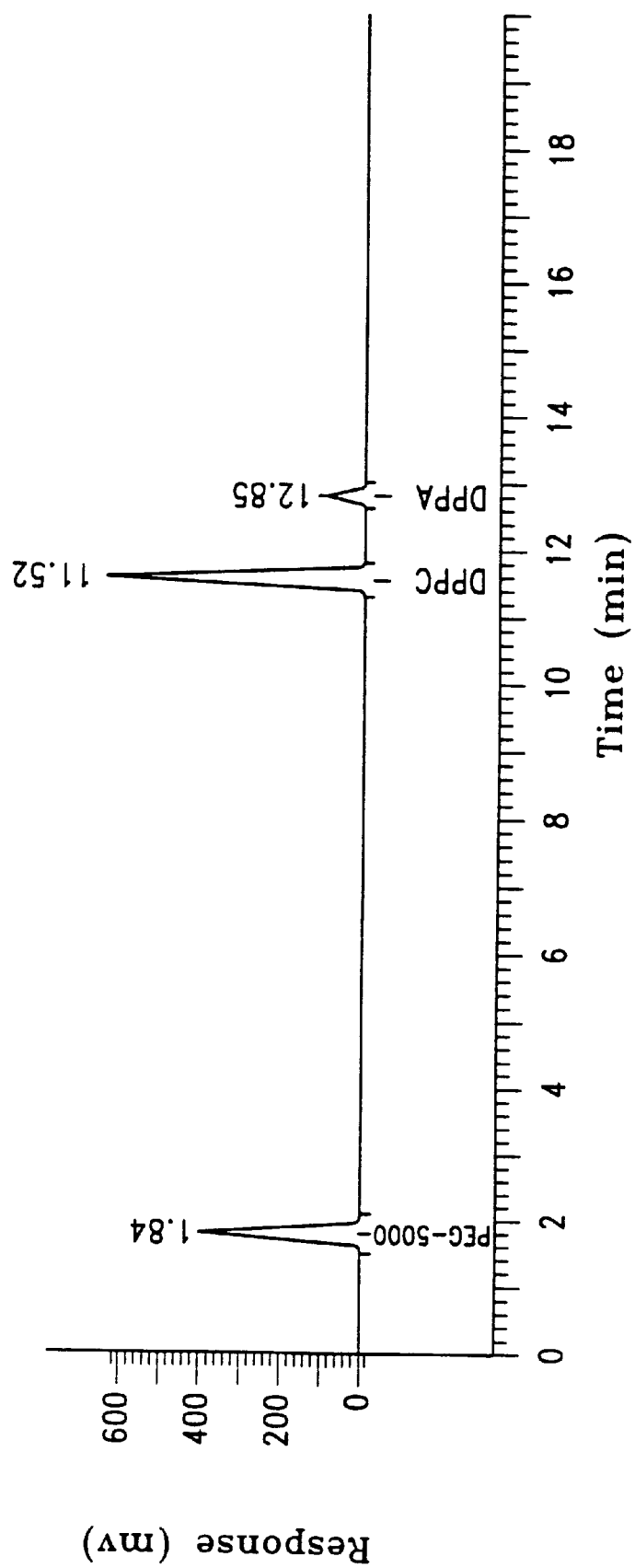
FIG. 1 displays high pressure liquid chromatography (HPLC) profile using a non-linear gradient. HPLC separations were performed with an ASTEC 5 μm spherical diol-bonded 250×4.6 mm steel analytical column (Advanced Separation Technologies, Inc., Whippany, N.J.). The mobile phase for development consisted of a chloroform:methanol:30% aqueous ammonia mixture (90:9:1.0, v:v:v) and an enrichment phase consisting of chloroform:methanol:water:30% aqueous ammonia mixture (60:34:4.0:2.0, v:v:v:v).

As employed above and throughout the disclosure, the following terms, unless otherwise indicated, shall be understood to have the following meanings.

"Lyophilize" refers to the preparation of a lipid composition in dry form by rapid freezing and dehydration in the frozen state (sometimes referred to as sublimation). Lyophilization takes place at a temperature which results in the crystallization of the lipids to form a lipid matrix. This process may take place under vacuum at a pressure sufficient to maintain frozen product with the ambient temperature of the containing vessel at about room temperature, preferably less than about 500 mTorr, more preferably less than about 200 mTorr, even more preferably less than about 1 mTorr. Due to the small amount of lipids used to prepare the lipid composition of the present invention, lyophilization is not difficult to conduct. The lipid composition in the present invention is an improvement over conventional microsphere compositions because the amount of lipids are reduced in comparison to the prior art and the lipid composition is formulated to minimize loss due to filtration of large (>0.22 μm) particulate matter. The latter is particularly important with lipids having a net negative charge (i.e. phospatidic acid) because their solubility in aqueous-based diluents is marginal.

"Reconstituting" refers to restoring the original composition by adding an aqueous carrier to the original parts. Thus, adding an aqueous carrier to the lyophilized 82% DPPC:8% DPPE-PEG:10% DPPA (mole %) reconstitutes the original lipid blend.

The lyophilized lipid composition produced in accordance with the methods of the present invention has a uniform ratio of lipids throughout the composition. Thus, the consistency of the ratio of lipids provides ease in reconstituting the composition in an aqueous-based pharmaceutically acceptable carrier. The ratio of dipalmitoylphosphatidylcholine, dipalmitoylphosphatidylethanolamine-polyethylene glycol, and dipalmitoylphosphatidic acid of about 70 to about 90 mole percent, about 5 to about 15 mole percent, and about 5 to about 15 mole percent, respectively, is the same in different parts of the lyophilized lipid composition. This typically insures consistent sampling throughout the lipid composition and results in microspheres which are similar, if not identical, in lipid composition, and thus have improved properties. In addition, the preferred lyophilized lipid composition is flocculent, having a flaky powder appearance.

The uniform ratio of lipids throughout the composition is due, it is believed, at least in part on the three step process of preparing a lyophilized lipid composition involving hydration of the lipid in an aqueous-based carrier thereby establishing the proper physical matrix for the blend, freezing of the matrix, and removing the water from the matrix by drying.

Unexpectedly as a result of the uniform distribution of lipids in the composition and ease of reconstitution in an aqueous carrier, the gas-filled microspheres prepared in accordance with the methods of the present invention possess a number of surprising yet highly beneficial characteristics. For example, gas-filled microspheres are advantageous due to their biocompatibility and the ease with which lipophilic compounds can be made to cross cell membranes after the microspheres are ruptured. The microspheres of the invention also exhibit intense echogenicity on ultrasound, are highly stable to pressure, and/or generally possess a long storage life, either when stored dry or suspended in a liquid medium. The echogenicity of the microspheres is of importance to the diagnostic and therapeutic applications of the microspheres made according to the invention. The gas-filled microspheres also have the advantages, for example, of stable size, low toxicity and compliant membranes. It is believed that the flexible membranes of the gas-filled microspheres may be useful in aiding the accumulation or targeting of these microspheres to tissues such as the vasculature and tumors.

The gas-filled microspheres made according to the present invention thus have superior characteristics for ultrasound contrast imaging. When inside an aqueous or tissue media, the gas-filled microsphere creates an interface for the enhanced absorption of sound.

"Microsphere" refers to a spherical entity which is characterized by the presence of an internal void. Preferred microspheres are formulated from lipids, including the various lipids described herein. In any given microsphere, the lipids may be in the form of a monolayer or bilayer, and the mono- or bilayer lipids may be used to form one or more mono- or bilayers. In the case of more than one mono- or bilayer, the mono- or bilayers are generally concentric. The microspheres described herein include such entities commonly referred to as liposomes, micelles, bubbles, microbubbles, vesicles, and the like. Thus, the lipids may be used to form a unilamellar microsphere (comprised of one monolayer or bilayer), an oligolamellar microsphere (comprised of about two or about three monolayers or bilayers) or a multilamellar microsphere (comprised of more than about three monolayers or bilayers). The internal void of the microsphere is filled with a fluorine-containing gas; a perfluorocarbon gas, more preferably perfluoropropane or perfluorobutane; a hydrofluorocarbon gas; or sulfur hexafluoride; and may further contain a solid or liquid material, including, for example, a targeting ligand and/or a bioactive agent, as desired.

"Liposome" refers to a generally spherical cluster or aggregate of amphipathic compounds, including lipid compounds, typically in the form of one or more concentric layers. Most preferably the gas-filled liposome is constructed of a single layer (i.e. unilamellar) or a single monolayer of lipid. While the preferred liposome composition comprises dipalmitoylphosphatidylcholine, dipalmitoylphosphatidylethanolamine-polyethylene glycol, and dipalmitoylphosphatidic acid in a ratio of about 70 to about 90 mole percent, about 5 to about 15 mole percent, and about 5 to about 15 mole percent, respectively, a wide variety of lipids may be used to fabricate the liposomes including phospholipids and non-ionic surfactants (e.g. niosomes). Most preferably the lipids comprising the gas-filled liposomes are in the gel state at physiological temperature. The liposomes may be cross-linked or polymerized and may bear polymers such as polyethylene glycol on their surfaces. Targeting ligands directed to endothelial cells may be bound to the surface of the gas-filled liposomes. Most preferably the liposomes are substantially devoid of water in their interiors.

The present invention is directed, inter alia, to a lyophilized lipid composition comprising the lipids dipalmitoylphosphatidylcholine, dipalmitoylphosphatidylethanolamine-polyethylene glycol, and dipalmitoylphosphatidic acid in a ratio of about 70 to about 90 mole %, about 5 to about 15 mole %, and about 5 to about 15 mole %, respectively, wherein the combined concentration of lipids is about 20 mg/ml to about 50 mg/ml, more preferably about 40 mg/ml, more preferably about 30 mg/ml, even more preferably about 25 mg/ml of aqueous solution prior to lyophilizing.

Polyethylene glycol useful in the lipid composition and microspheres of the present invention may have a molecular weight of about 4,000 to about 200,000, more preferably about 1,000 to about 20,000, even more preferably about 2,000 to about 8,000, and most preferably about 5,000.

A gas-filled microsphere is also an embodiment of the present invention, which microsphere comprises a blend of the lyophilized lipids dipalmitoylphosphatidylcholine, dipalmitoylphosphatidylethanolamine-polyethylene glycol, and dipalmitoylphosphatidic acid in a ratio of about 70 to about 90 mole %, about 5 to about 15 mole %, and about 5 to about 15 mole %, respectively, and perfluorocarbon in an aqueous-based pharmaceutically acceptable carrier. The combined concentration of lipids is about 0.1 mg/ml to about 5 mg/ml of the pharmaceutically acceptable carrier. The preferred perfluorocarbons are perfluoropropane and perfluorobutane.

The present invention is also directed to a method of preparing the lyophilized lipid composition comprising dispersing the lipids dipalmitoylphosphatidylcholine, dipalmitoylphosphatidylethanolamine-polyethylene glycol, and dipalmitoylphosphatidic acid in a ratio of about 70 to about 90 mole %, about 5 to about 15 mole %, and about 5 to about 15 mole %, respectively in an aqueous solution to a concentration of about 20 mg/ml to about 50 mg/ml to form a lipid-containing aqueous solution; and lyophilizing the lipid-containing aqueous solution to form a lyophilized lipid composition such that the dipalmitoylphosphatidylcholine, dipalmitoylphosphatidylethanolamine-polyethylene glycol, and dipalmitoylphosphatidic acid ratio of about 70 to about 90 mole %, about 5 to about 15 mole %, and about 5 to about 15 mole %, respectively, is uniform throughout the composition.

The method of making a microsphere filled with a fluorine-containing gas is another embodiment of the present invention, which method comprises obtaining a lyophilized lipid composition comprising the lipids dipalmitoylphosphatidylcholine, dipalmitoylphosphatidylethanolamine-polyethylene glycol, and dipalmitoylphosphatidic acid, in a ratio of about 70 to about 90 mole percent, about 5 to about 15 mole percent, and about 5 to about 15 mole percent, respectively, wherein the combined concentration of lipids is about 20 mg/ml to about 50 mg/ml of aqueous solution prior to lyophilizing; dispersing the lyophilized composition in an aqueous-based pharmaceutically acceptable carrier to a concentration of about 0.1 mg/ml to about 5 mg/ml to form an aqueous microsphere-forming solution; introducing fluorine-containing gas into the aqueous microsphere-forming solution to form a fluorine-containing gas aqueous microsphere-forming solution; and shaking the aqueous microsphere-forming solution to form a fluorine-containing gas-filled microsphere.

An alternative method for preparing a microsphere filled with fluorine-containing gas of the present invention comprises reconstituting the lipids dipalmitoylphosphatidylcholine, dipalmitoylphosphatidylethanolaminepolyethylene glycol, and dipalmitoylphosphatidic acid in a ratio of about 70 to about 90 mole %, about 5 to about 15 mole %, and about 5 to about 15 mole %, respectively, in an aqueous solution to a concentration of about 20 mg/ml to about 50 mg/ml to form a lipid-containing aqueous solution; lyophilizing the lipid-containing aqueous solution to form a lyophilized composition such that the dipalmitoylphosphatidylcholine, dipalmitoylphosphatidylethanolamine-polyethylene glycol, and dipalmitoylphosphatidic acid ratio of about 70 to about 90 mole %, about 5 to about 15 mole %, and about 5 to about 15 mole %, respectively, is uniform throughout the composition; dispersing the lyophilized composition in an aqueous pharmaceutically acceptable carrier to a concentration of about 0.1 mg/ml to about 5 mg/ml to form an aqueous microsphere-forming solution; introducing a fluorine-containing gas into the aqueous microsphere-forming solution; and shaking the aqueous microsphere-forming solution to form a fluorine-containing gas-filled microsphere.

The aqueous carrier of the lipid composition may be water, buffer, normal saline, physiological saline, and the like, as well as other aqueous carriers readily apparent to those skilled in the art. The pharmaceutically acceptable aqueous-based carrier of the microsphere solution may be water, buffer, normal saline, physiological saline, a mixture of water, glycerol, and propylene glycol or a mixture of saline, glycerol, and propylene glycol where the components of the mixtures are in a ratio of 8:1:1 or 9:1:1, v:v:v, a mixture of saline and propylene glycol in a ratio of 9:1, v:v, and the like.

In still further embodiments, the present invention comprises novel methods of making the gas-filled microspheres, which methods include those set forth above and may further comprise filtering the aqueous microsphere-forming solution, extruding the aqueous microsphere-forming solution through at least one filter of a selected pore size, where the pore size may be smaller than 10 µm, preferably about 0.22 µm. In yet another embodiment, the aqueous microsphere-forming solution may be heated. The methods of making a gas-filled microsphere include placing a vessel containing the aqueous microsphere-forming solution in a chamber, which chamber may be pressurized, introducing perfluorocarbon into said chamber such that the head space of the vessel is filled with perfluorocarbon, and shaking the vessel to form perfluorocarbon-containing microsphere.

The preferred method for preparing the lipid composition comprises dispersing the lipids dipalmitoylphosphatidylcholine, dipalmitoylphosphatidylethanolamine-polyethylene glycol, and dipalmitoylphosphatidic acid in a ratio of about 82 mole %, about 8 mole %, and about 10 mole %, respectively, in an aqueous solution to a concentration of about 25 mg/ml to form a lipid-containing aqueous solution; and lyophilizing the lipid-containing aqueous solution to form a lyophilized lipid composition such that the dipalmitoylphosphatidylcholine, dipalmitoylphosphatidylethanolamine-polyethylene glycol, and dipalmitoylphosphatidic acid ratio of about 82 mole %, about 8 mole %, and about 10 mole %, respectively, is uniform throughout the composition.

Preferred methods for preparing the gas-filled microspheres comprise dispersing the lipids dipalmitoylphosphatidylcholine, dipalmitoylphosphatidylethanolaminepolyethylene glycol, and dipalmitoylphosphatidic acid in a ratio of about 82 mole %, about 8 mole %, and about 10 mole %, respectively, in an aqueous solution to a concentration of about 25 mg/ml to form a lipid-containing aqueous solution; lyophilizing the lipid-containing aqueous solution to form a lyophilized lipid composition such that the dipalmitoylphosphatidylcholine, dipalmitoylphosphatidylethanolamine-polyethylene glycol, and dipalmitoylphosphatidic acid ratio of about 82 mole %, about 8 mole %, and about 10 mole %, respectively, is uniform throughout the composition; dispersing the composition in an aqueous-based pharmaceutically acceptable carrier to a concentration of about 1 mg/ml to form an aqueous microsphere-forming solution in a vessel; filtering the aqueous microsphere-forming solution through a sterile filter having pores of about 0.22 µm; optionally heating the aqueous microsphere-forming solution; dispersing the aqueous microsphere-forming solution into at least one vessel, placing the vessel into a pressurized chamber and evacuating the chamber; introducing a fluorine-containing gas into the chamber such that the head space of the vessel is filled with a fluorine-containing gas, and shaking the vessel. Preferably, the vessel is shaken at a temperature below the gel to liquid crystalline phase transition temperature of the lipid to form a fluorine-containing gas-filled microsphere.

Lyophilized Lipid Composition

The lyophilized lipid composition of the particularly preferred embodiments of the present invention comprises three components: (1) dipalmitoylphosphatidylcholine, a neutral (e.g., nonionic or zwitterionic) lipid, (2) dipalmitoylphosphatidylethanolamine-polyethylene glycol, a lipid bearing a hydrophilic polymer, and (3) dipalmitoylphosphatidic acid, a negatively charged lipid. Preferably, the amount of the negatively charged lipid will be greater than 1 mole percent of total lipid present, and the amount of lipid bearing a hydrophilic polymer will be greater than 1 mole percent of total lipid present. The process of using two or more lipids may be quite advantageous, especially when using a lipid that is not soluble in aqueous-based carriers by itself. Water insoluble lipids such as phosphatidic acid can be made to disperse more easily in aqueous-based carriers when they are first prepared in combination with another lipid (or lipids) by the aqueous dispersion, lyophilization method of the present invention.

It has also been found advantageous to achieving the stabilized microspheres of the present invention that they preferably be prepared at a temperature below the gel to liquid crystalline phase transition temperature of a lipid used as the stabilizing compound, and this such preparation is preferred. This phase transition temperature is the temperature at which a lipid bilayer will convert from a gel state to a liquid crystalline state. See, for example, Chapman et al., *J. Biol. Chem.* 1974 249, 2512–2521.

It is believed that, generally, the higher the gel state to liquid crystalline state phase transition temperature, the more impermeable the gas-filled microspheres are at any given temperature. See Derek Marsh, *CRC Handbook of Lipid Bilayers* (CRC Press, Boca Raton, Fla. 1990), at p. 139 for main chain melting transitions of saturated diacyl-sn-glycero-3-phosphocholines. The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984).

A small amount, i.e., about 1 to about 15 mole percent of the total lipid, of the negatively charged lipid dipalmitoylphosphatidic acid from which the gas-filled microspheres are to be formed, lends enhanced stability to the microspheres of the present invention. The negatively charged lipid, dipalmitoylphosphatidic acid, may provide added stability by counteracting the tendency of the microspheres to rupture by fusing together, i.e., the negatively charged lipids tend to establish a uniform negatively charged layer on the outer surface of the microsphere, which will be repulsed by a similarly charged outer layer on the other microspheres. In this way, the microspheres will tend to be prevented from coming into touching proximity with each other, which would often lead to a rupture of the membrane or skin of the respective microspheres and consolidation of the contacting microspheres into a single, larger microsphere. A continuation of this process of consolidation will, of course, lead to significant degradation of the microspheres.

Lipids which may be used to prepare the gas-filled microspheres used in the present invention include but are not limited to lipids such as dipalmitoylphosphatidylcholine (DPPC), dipalmitoylphosphatidylethanolamine-polyethylene glycol (DPPE-PEG), and dipalmitoylphosphatidic acid (DPPA). The above-identified lipids are in a ratio of about 70 to about 90 mole percent, about 5 to about 15 mole percent, and about 5 to about 15 mole percent, respectively, more preferably about 80 to about 85 mole percent, about 5 to about 10 mole percent, and about 5 to about 10 mole percent, respectively, and most preferably about 82 mole percent, about 8 mole percent, and about 10 mole percent, respectively. The ratio of lipids in the lipid composition and microsphere of the present invention is consistent throughout the composition and microsphere.

The total concentration of lipids in the lyophilized lipid composition is about 20 to about 50 mg/ml, more preferably about 30 mg/ml even more preferably about 25 mg/ml. Significantly, the lipid concentration results in a mixture or blend of lipids. For purposes of the present invention a lyophilized lipid composition preferably have at least about 50% dispersed lipids, preferably at least about 60% dispersed lipids, more preferably at least about 70% dispersed lipids, even more preferably at least about 80% dispersed lipids, and most preferably at least about 90% dispersed lipids. Once prepared, the lyophilized lipid composition of the present invention is then useful in preparing gas-filled microspheres. The concentration of lipids in the microsphere is about 0.1 to about 2 mg/ml, and even more preferably about 1 mg/ml. Importantly, the lipid concentration in the microsphere preparation permits the formation of gas-filled microspheres and is substantially devoid of liquid-filled microspheres. Substantially devoid of liquid-filled microspheres for purposes of the present invention refers a microsphere composition having at least 50% gas-filled microspheres, preferably at least about 60% gas-filled microspheres, more preferably at least about 70% gas-filled microspheres, even more preferably at least about 80% gas-filled microspheres and most preferably at least about 90% gas-filled microspheres.

A particularly desired component of the stabilized gas-filled microspheres is an aqueous environment of some kind, which induces the lipid, because of its hydrophobic/hydrophilic nature, to form microspheres, the most stable configuration which it can achieve in such an environment. The carriers or diluents which can be employed to create such an aqueous environment include, but are not limited to water, either deionized or containing any number of dissolved salts, etc., which will not interfere with creation and maintenance of the microspheres or their use; and normal saline and physiological saline, and the like. The concentration of lipids to aqueous carrier in the lipid composition prior to lyophilizing is about 20 to about 50 mg/ml, more preferably about 25 mg/ml.

Preferred embodiments of the lyophilized lipid composition contemplated by the present invention would include dipalmitoylphophatidylcholine (DPPC), dipalmitoylphosphatidylethanolamine-polyethylene glycol-5000 (DPPE-PEG5000), and dipalmitoylphosphatidic acid (DPPA). These compositions in a 82:8:10 ratio of mole percentages, respectively, are most preferred. The DPPC component is effectively neutral, since the phosphatidyl portion is negatively charged and the choline portion is positively charged. The second component, DPPE-PEG in the concentration range of the ultimate gas-filled microsphere, provides a polyethylene glycol bound to the lipid by the DPPE moiety, with the PEG moiety free to surround the resulting microsphere membrane or skin, and thereby form a physical barrier to various enzymatic and other endogenous agents in the body whose function is to degrade such foreign materials. The DPPE-PEG provides more microspheres of a smaller size, upon rehydration of the lipid composition, which are safe and stable to pressure when combined with other lipids such as DPPC and DPPA in the given ratios. It is also theorized that PEG is able to defeat the action of the macrophages of the human immune system, which would otherwise tend to surround and remove the foreign object. The result is an increase in the time during which the microspheres can function as diagnostic imaging contrast media. The DPPA component, which is negatively charged, is added to enhance stabilization in accordance with the mechanism described further above regarding negatively charged lipids as an additional agent.

Gas-Filled Microspheres

The microspheres of the invention encapsulate a gas. The term "gas-filled", as used herein, means that the microspheres to which the present invention is directed, have an interior volume that is comprised of at least about 10% gas, preferably at least about 25% gas, more preferably at least about 50% gas, even more preferably at least about 75% gas, and most preferably at least about 90%. In use, where the presence of gas is important, it is preferred that the interior microsphere volume comprise at least about 10% gas, preferably at least about 25%, 50%, 75%, and most preferably at least about 90% gas.

In particular, fluorine-containing gases including perfluorocarbons, hydrofluorocarbons, and sulfur hexafluoride have been found to be suitable for use in the gas-filled microspheres of the present invention. Suitable perfluorocarbons include, for example, perfluorobutane, perfluorocyclobutane, perfluoromethane, perfluoroethane, perfluoropropane, perfluoropentane, perfluorohexane, most preferably perfluoropropane. Suitable hydrofluorocarbons include 1,1,1,2,3,3,3 heptafluoropropane and 1,1,2,2,3,3,3 heptafluoropropane. Also preferred are a mixture of different types of gases, such as a perfluorocarbon gas and another type of gas such as air, oxygen, and the like. Indeed, it is believed that a combination of gases may be particularly useful in diagnostic imaging applications.

The perfluorocarbon gases are biocompatible gases. By "biocompatible" is meant a gas which, when introduced into the tissues of a human patient, will not result in any degree of unacceptable toxicity, including allergenic responses and disease states, and preferably are inert. Such a gas should also be suitable for making gas-filled microspheres, as described herein.

Stabilizing compounds described in U.S. patent application Ser. No. 160,232 and 159,687 may be employed. The size of the microspheres can thereby be adjusted for the particular intended diagnostic imaging end use. The size of the microspheres is preferably about 30 nanometers to about 100 microns in diameter, more preferably between 100 nanometers to about 10 microns in diameter, even more preferably 200 nanometers to about 7 microns in diameter. For particular uses, magnetic resonance imaging of the vasculature, for example, may require microspheres that are no larger that about $30\mu$ in diameter, and that are preferably smaller, e.g., no larger than about 12μ in diameter. The size of the gas-filled microspheres can be adjusted, if desired, by a variety of procedures including microemulsification, vortexing, extrusion, filtration, sonication, homogenization, repeated freezing and thawing cycles, extrusion under pressure through pores of defined size, and similar methods.

For intravascular use the microspheres are generally under 30μ in mean diameter, and are preferably under about 12μ in mean diameter. For targeted intravascular use, e.g., to bind to a certain tissue such as endothelial tissue, the microspheres can be appreciably under a micron, even under 100 nm diameter.

Methods of Preparation

The lyophilized lipid composition and gas-filled microspheres of the present invention may be prepared by a number of suitable methods. These are described below separately for each case.

The lyophilized lipid composition of the present invention is prepared by a method comprising dispersing lipids in an aqueous-based solution, and lyophilizing the lipid-containing aqueous-based solution to form a composition such that the ratio of lipids in the lipid composition is consistent throughout the composition. The first step in the process of making the lyophilized lipid composition is dispersing or dissolving the lipids in an aqueous-based solution or suspension. The lipids dipalmitoylphosphatidylcholine, dipalmitoylphosphatidylethanolamine-polyethylene glycol, and dipalmitoylphosphatidic acid are added to an aqueous-based solution such as water, physiological saline, normal saline, and the like. The total lipid concentration in the aqueous-based solution is about 20 mg/ml to about 30 mg/ml, more preferably about 25 mg/ml.

The step of lyophilizing the aqueous-based lipid solution includes freezing and dehydration. The sample is frozen and dehydrated at a temperature of from about −50° C. to about 25° C., preferably from about −20° C. to about 25° C., even more preferably from about 10° C. to about 25° C. This temperature range includes and is not limited to placing the lipid solution on dry ice and in liquid nitrogen. The lyophilization preferably takes place under vacuum, at a pressure sufficient to maintain frozen product with the ambient temperature of the containing vessel at about room temperature, preferably less than about 1 mTorr.

For large preparations of lipid compositions, such as about two liters at a concentration of about 25 mg/ml, the lyophilization step takes about 16 hours to about 72 hours, more preferably about 24 hours to about 96 hours, even more preferably about 16 hours to about 24 hours to complete. As a result of lyophilization, the composition is easy to redisperse in another aqueous carrier, such as a pharmaceutically acceptable carrier. Lyophilization also contributes, in whole or in part, to the consistency of the ratio of lipids throughout the composition. The ratio of about 70 to about 90 mole % dipalmitoylphosphatidylcholine, about 5 to about 15 mole % dipalmitoylphosphatidylethanolamine-polyethylene glycol, and about 5 to about 15 mole % dipalmitoylphosphatidic acid is distributed uniformly across the resulting lipid composition.

While not intending to be bound by any particular theory of operation, the present invention is believed to rely, at least in part, on the three step process of preparing a lyophilized lipid composition involving hydration of the lipid in an aqueous-based carrier thereby establishing the proper physical matrix for the blend, freezing of the matrix, and removing the water from the matrix by drying. The resultant lipid composition may be stored in the dry form and/or may then be dispersed in aqueous-based carrier, such as formulations for diagnostic and pharmaceutical use.

The preferred embodiment of the composition of the present invention is a flocculent powder of lyophilized lipids. For purposes of the present invention "flocculent" refers to a fluffy or flaky appearance of the lipid composition. The flocculent form is preferred because its ease of reconstitution and in the preparation of the gas-filled microspheres of the invention. The resulting lyophilized composition may be reconstituted by rehydrating the composition in an aqueous-based carrier, such as a pharmaceutically acceptable vehicle. A pharmaceutically acceptable carrier or vehicle is an aqueous-based carrier or vehicle which provides no toxic side effects when administered in the proper dose range. Alternatively, the lyophilized composition may be retained in a dry form, such as a powder. The shelf life of the dry form is about one years to about two years.

In the preparation of a gas-filled microsphere of the present invention, the lyophilized lipid composition is first prepared in accordance with the methods set forth herein. The lyophilized lipid composition is rehydrated or dispersed in a pharmaceutically acceptable aqueous carrier to form an aqueous microsphere-forming solution, a fluorine-containing gas is introduced into said aqueous microsphere-forming solution, and the solution is agitated.

The lyophilized lipid composition is easily dispersed into the pharmaceutically acceptable carrier in view of the uniform distribution of the lipid ratio throughout the composition. Pharmaceutically acceptable carriers include and are not limited to water, saline, a mixture of water:propylene glycol:glycerol or a mixture of saline:propylene glycol:glycerol, wherein the mixtures are preferably in a ratio of about 9:1:1 (v:v:v), or more preferably about 8:1:1 (v:v:v), saline:propylene glycol in a ratio of about 9:1 (v:v), and saline:glycerol 9:1 (v:v), and the like. Propylene glycol may facilitate dispersion or dissolution of the lipids. The propylene glycol may also function as a thickening agent which improves microsphere formation and stabilization by altering the surface tension on the microsphere membrane or skin. It is possible that the propylene glycol further functions as an additional layer that coats the membrane or skin of the microsphere, thus providing additional stabilization.

Thus, the rehydrated lipid composition, now an aqueous microsphere-forming solution, comprises dipalmitoylphosphatidylcholine, dipalmitoylphosphatidylethanolaminepolyethylene glycol, and dipalmitoylphosphatidic acid in a ratio of about 70 to about 90 mole %, about 5 to about 15 mole %, and about 5 to about 15 mole %, respectively. The concentration of the lipid composition in the pharmaceutically acceptable carrier, however, is now about 0.1 mg/ml to about 5 mg/ml, more preferably about 3.0 mg/ml, and more preferably about 1.0 mg/ml.

The next step is introduction of the fluorine-containing gas into the aqueous microsphere-forming solution to form a fluorine-containing gas aqueous microsphere-forming solution. Most preferably the liposomes are substantially devoid of water in their interiors. Substantially devoid of water in their interiors refers to microspheres to which the present invention is directed, having an interior volume that is comprised of at least about 10% gas, preferably at least about 25% gas, more preferably at least about 50% gas, even more preferably at least about 75% gas, and most preferably at least about 90% gas. In use, where the presence of gas is important, it is preferred that the interior microsphere volume comprise at least about 10% gas, preferably at least about 25%, 50%, 75%, and most preferably at least about 90% gas.

In the preferred embodiment, the fluorine-containing gas, preferably a perfluorocarbon gas, more preferably perfluoropropane or perfluorobutane, displaces the air in the head space above the aqueous microsphere-forming solution as to form gas-filled microspheres which entrap the perfluorocarbon gas, ambient gas (e.g., air), or coentrap perfluorocarbon gas and ambient air, upon shaking.

The perfluorocarbon-containing aqueous microsphere-forming solution is then agitated to form a gas-filled microsphere. A preferred embodiment comprises the steps of agitating an aqueous solution comprising the lyophilized lipid composition, in the presence of perfluorocarbon at a temperature below the gel to liquid crystalline phase transition temperature of the lipid to form the gas-filled microsphere of the present invention.

The terms agitation, shaking, and variations thereof, as used herein, means any motion that agitates an aqueous solution such that gas is introduced from the local ambient environment into the aqueous solution. The shaking must be of sufficient force to result in the formation of microspheres. The shaking may be by swirling, such as by vortexing, side-to-side, or up-and-down motion. Different types of motion may be combined. Also, the shaking may occur by shaking the container holding the aqueous lipid solution, or by shaking the aqueous solution within the container without shaking the container itself.

Further, the shaking may occur manually or by machine. Mechanical shakers that may be used include, for example, a shaker table such as a VWR Scientific (Cerritos, Calif.) shaker table, a WIG-L-BUG™ Shaker from Crescent Dental Mfg. Ltd., Lyons, Ill., an ESPE Capmix™, (Seefeld-Oberweis, Germany) and DeGussa Mix-o-Mat (Frankfurt, Germany). It is a preferred embodiment of the present invention that certain modes of shaking or vortexing be used to make stable microspheres within a preferred size range. Shaking is preferred, and it is preferred that this shaking be carried out using the ESPE Capmix™ mechanical shaker. In accordance with this preferred method, it is preferred that a reciprocating motion be utilized to generate the gas-filled microspheres. It is a preferred embodiment of the present invention that the number of reciprocations, i.e., full cycle oscillations, be within the range of about 1000 and about 20,000 per minute. More preferably, the number of reciprocations or oscillations will be between 2500 and 8000. Even more preferably, the number of reciprocations or oscillations of the WIG-L-BUG™ is greater than 2600. The WIG-L-BUG™, referred to above, is a mechanical shaker which provides 6000 oscillations every minute. Of course, the number of oscillations is dependent upon the mass of the contents being agitated, (with the larger the mass, the fewer the number of oscillations). The ESPE Capmix™ provides about 4300 reciprocations per minute (RPM). Another means for producing shaking includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing at least 60–300 revolutions per minute is more preferred. Vortexing at 300–1800 revolutions per minute is most preferred. The formation of gas-filled microspheres upon shaking can be detected visually. The concentration of lipid required to form a desired stabilized microsphere level will vary depending upon the type of lipids used, and may be readily determined by routine experimentation. For example, in preferred embodiments, the concentration of the blend of lyophilized lipids used to form stabilized microspheres according to the methods of the present invention is about 0.1 mg/ml to about 5 mg/ml of saline solution, more preferably from about 1 mg/ml to about 3 mg/ml of saline solution, and most preferably from about 1 mg/ml of saline solution.

The size of gas-filled microspheres can be adjusted, if desired, by a variety of procedures including microemulsification, vortexing, extrusion, filtration, sonication, homogenization, repeated freezing and thawing cycles, extrusion under pressure through pores of defined size, and similar methods. It may also be desirable to use the microspheres of the present invention as they are formed, without any attempt at further modification of the size thereof.

Additional optional steps may be incorporated into the method of making a gas-filled microsphere in accordance with the present invention. The additional steps include heating and filtering which may be for sterilization or sizing. These steps may be performed at various stages of the method, preferably, but not limited to, prior to the formation of an aqueous microsphere-forming solution and following shaking the gas-containing aqueous microsphere-forming solution.

The gas-filled microspheres may be sized by a simple process of extrusion through filters; the filter pore sizes control the size distribution of the resulting gas-filled microspheres. By using two or more cascaded, i.e., a stacked set of filters, e.g., $10\mu$ followed by $8\mu$, the gas-filled microspheres have a very narrow size distribution centered around 7–9 $\mu$m. After filtration, these stabilized gas-filled microspheres remain stable for over 24 hours.

The sizing or filtration step optionally may be accomplished by the use of a filter assembly when the suspension is removed from a sterile vial prior to use, or even more preferably, the filter assembly may be incorporated into a syringe during use. The method of sizing the microspheres will then comprise using a syringe comprising a barrel, at least one filter, and a needle; and will be carried out by a step of extracting which comprises extruding said microspheres from said barrel through said filter fitted to said syringe between said barrel and said needle, thereby sizing said microspheres before they are administered to a patient in the course of using the microspheres as ultrasound contrast agents in accordance with the present invention. The step of extracting may also comprise drawing said microspheres into said syringe, where the filter will function in the same way to size the microspheres upon entrance into the syringe. Another alternative is to fill such a syringe with microspheres which have already been sized by some other means, in which case the filter now functions to ensure that only microspheres within the desired size range, or of the desired maximum size, are subsequently administered by extrusion from the syringe. The syringe may then administer sized microspheres directly to a patient, or may disperse the microspheres into a vessel.

Typical of the devices which can be used for carrying out the sizing or filtration step, is the syringe and filter combination shown in FIG. 2 of U.S. Ser. No. 08/401,974, filed Mar. 9, 1995, the disclosure of which is hereby incorporated by reference in its entirety.

The stabilizing compound solution or suspension may be extruded through a filter. Optionally the said solution or suspension may be heat sterilized prior to shaking. Heating may also assist in dispersing the lipids in the carrier. The step of heating in the method of making gas-filled microspheres of the present invention, while preferred, is optional. Once gas-filled microspheres are formed, they may be filtered for sizing as described above. These steps prior to the formation of gas-filled microspheres provide the advantages, for example, of reducing the amount of unhydrated stabilizing compound, and thus providing a significantly higher yield of gas-filled microspheres, as well as and providing sterile gas-filled microspheres ready for administration to a patient. For example, a mixing vessel such as a vial or syringe may be filled with a perfluorocarbon-containing microsphere suspension, and the suspension may then be sterilized within the mixing vessel, for example, by autoclaving. Gas may be instilled into the lipid suspension to form gas-filled microspheres by shaking the sterile vessel. Preferably, the sterile vessel is equipped with a filter positioned such that the gas-filled microspheres pass through the filter before contacting a patient.

Extruding the solution through a filter, decreases the amount of unhydrated compound by breaking up the dried compound and exposing a greater surface area for hydration.

Preferably, the filter has a pore size of about 0.1 to about 5 µm, more preferably, about 0.1 to about 4 µm, even more preferably, about 0.1 to about 2 µm, and most preferably, about 1 µm. Unhydrated compound appears as amorphous clumps of non-uniform size and is undesirable.

Sterilization, provides a composition that may be readily administered to a patient for ultrasound. Preferably, sterilization is accomplished by filtration. Optionally, heat sterilization may take place by autoclaving the solution at a temperature of at least about 100° C., and more preferably, by autoclaving at about 100° C. to about 130° C., even more preferably, about 110° C. to about 130° C., even more preferably, about 120° C. to about 130° C., and most preferably, about 130° C. Preferably, heating occurs for at least about 1 minute, more preferably, about 1 to about 30 minutes, even more preferably, about 10 to about 20 minutes, and most preferably, about 15 minutes.

Where sterilization occurs by a process other than heat sterilization at a temperature which would cause rupture of the gas-filled microspheres, sterilization may occur subsequent to the formation of the gas-filled microspheres. For example, gamma radiation may be used before and/or after gas-filled microspheres are formed.

In addition, the fluorine-containing gas may be introduced into the aqueous microsphere-forming solution placing a vessel containing the aqueous microsphere-forming solution in a chamber and introducing perfluorocarbon gas. The vessel is subsequently shaken to form a fluorine-containing gas-filled microsphere. Alternatively, the vessel containing the aqueous microsphere-forming solution may be placed in a pressurized chamber, the chamber evacuated of gas and filled with a fluorine-containing gas such that the head space of the vessel is filled with a fluorine-containing gas. Again, the vessel may be shaken to form a fluorine-containing gas-filled microsphere. These steps may be performed without placing the vessel in a chamber as well. Instead, the vessel containing the aqueous microsphere-forming solution may be filled with a fluorine-containing gas to accommodate the head space, followed by shaking the vessel. The preferred fluorine-containing gases are perfluorocarbon gases, more preferably perfluoropropane and perfluorobutane.

Methods of Use

The novel lyophilized lipid composition is useful in the preparation of the novel gas-filled microspheres of the present invention.

The novel gas-filled microspheres, useful as contrast media in diagnostic imaging, will be found to be suitable for use in all areas where diagnostic imaging is employed.

In accordance with the present invention there is provided a method of imaging a patient generally, and/or in specifically diagnosing the presence of diseased tissue in a patient. The imaging process of the present invention may be carried out by administering a contrast medium comprising the gas-filled microspheres of the invention to a patient, and then scanning the patient using magnetic resonance imaging, for example, to obtain visible images of an internal region of a patient and/or of any diseased tissue in that region. By region of a patient, it is meant the whole patient or a particular area or portion of the patient. In addition, the present invention provides a method of diagnosing the presence of diseased tissue in a patient.

As one skilled in the art would recognize, administration of the stabilized gas-filled microspheres used in the present invention may be carried out in various fashions, such as intravascularly, orally, rectally, etc., using a variety of dosage forms. When the region to be scanned is the cardiovascular region, for example, administration of the contrast medium comprising the gas-filled microspheres of the invention is preferably carried out intravascularly. When the region to be scanned is the gastrointestinal region, for example, administration of the contrast medium of the invention is preferably carried out orally or rectally. The useful dosage to be administered and the particular mode of administration will vary depending upon the age, weight and the particular mammal and region thereof to be scanned, and the particular contrast medium of the invention to be employed. Typically, dosage is initiated at lower levels and increased until the desired contrast enhancement is achieved. Various combinations of the stabilized gas-filled microspheres may be used to modify the relaxation behavior of the medium or to alter properties such as the viscosity, osmolarity or palatability (in the case of orally administered materials).

The invention is further demonstrated in the following actual Examples I–VII. The examples, however, are not intended to in any way limit the scope of the present invention.

EXAMPLES

Example 1

Demonstration of The Lipid Preparation Method

Sixty grams of dipalmitoylphosphatidylcholine (DPPC) was dispersed in sterile water U.S.P. to a final concentration of 25 mg/ml. The lipid was then heated to 45° C. for ten minutes followed by equilibration back to room temperature. The resultant dispersion was then lyophilized by freezing over an isopropanol/$CO_2$ bath or an acetone/$CO_2$ bath and drying on a Virtis Lyophilizer until the product appeared dry and flocculent in appearance. The dried flocculent product was then added to a pharmaceutical preparation comprised of 90% normal saline (0.9% NaCl):10% propylene glycol (Mallinckrodt, St. Louis, Mo., U.S.P.) resulting in a formulation having a lipid concentration of 5 mg/ml. The mixture was then heated to 45° C. for 10 minutes followed by filtration through two 0.2 µm Gelman Suporflow 200 sterilizing filters (Gelman Sciences, Ann Arbor, Mich.). The filtered product was clear in appearance and less than 0.1% by weight of residual lipid remained on the filter.

Example 2

Demonstration of the Preparation of a Mixture of Lipids

Sixty grams of lipid composed of 90%:10%, w:w, of dipalmitoylphosphatidylcholine (DPPC) and dipalmitoylphosphatidic acid (DPPA) were dispersed in sterile water U.S.P. to a final concentration of 25 ml per gram lipid (40 mg/ml), as described in Example 1. The identical procedure was used as described but the final lipid concentration in the formulation was 1 mg/ml. The product was filtered with less than 0.1% loss of residual lipid.

Example 3

Demonstration of the Preparation of a Mixture of Lipids

Sixty grams of lipid composed of 82%:8%:10% (mole %) (54%:40%:6% (weight %)), of dipalmitoylphosphatidylcholine (DPPC), dipalmitoylphosphatidylethanol-polyethylene glycol 5000 (DPPE-PEG 5000), and dipalmitoylphosphatidic acid (DPPA) were dispersed in sterile water U.S.P. to a final concentration of 25 ml per gram lipid, as described in Example 1. The same dispersion and lyophilization process was performed as described in Example 1. The lipid mixture was then dispersed in a pharmaceutical carrier comprised of 0.9% saline in sterile water:propylene glycol:glycerol, 8:1:1, (v:v:v) to a concentration of 25 mg/ml. The product was easily filtered, once again leaving less than 0.1% loss of the residual mixture.

Example 4

Comparison of Lipid Blends Formulated by Dispersion and Lyophilization in: 1) Ethanol:Cyclohexane, 2) Tertiary Butanol, and 3) an Aqueous Solvent Samples of lipid blends as described in Example 3 were prepared by dispersion in the three solvents: 1) ethanol:cyclohexane, 2) tertiary butanol (t-butanol or 1,1-dimethyl ethanol), and 3) water, followed by lyophilization as described in Example 1. Ethanol:cyclohexane (1:1, v:v) and t-butanol provide examples of organic solvents. Samples of each blend were then formulated in a pharmaceutical carrier comprised of 0.9% saline in sterile water-:propylene glycol:glycerol, 8:1:1, (v:v:v) as described in Example 3 to a concentration of 1 mg total lipid per ml carrier solution. Samples were sealed in vials and a headspace of not less than 65% by volume perfluoropropane was added. Samples were then agitated to form microspheres by placing the vials on a Wig-L-Bug™ (Crescent Dental, Lyons, Ill.) and shaking at a rate of 3300 rpm for 60 seconds. Each vial was then analyzed for microsphere concentration using a Particle Sizing Systems Model 770 (Particle Sizing Systems, Santa Barbara, Calif.) light obscuration particle sizer. Table 1 sets forth the distributions of the ethanol:cyclohexane blend, the tert-butanol blend, and the aqueous blend. Somewhat similar size distributions resulted for each blend. However, a superior number of microspheres was generated from the aqueous lipid mixture vs. the organic mixtures.

TABLE 1

Analytical Distribution for Microsphere Preparations from Cyclohexane-Ethanol, t-Butanol, and Aqueous Blends

| Microsphere Criteria | Cyclohexane-Ethanol Blend | *t-Butanol Blend | Aqueous Blend |
|---|---|---|---|
| Number Weighted Mean of Microsphere Size | 2.63 μm | 2.04 μm | 2.35 μm |
| Microspheres/ml | $8.33 \times 10^8$ | $1 \times 10^9$ | $1.6 \times 10^9$ |
| % Microspheres Below 10 μm | 96.88% | 99.3% | 99.31% |

*Note: The dispersion of t-butanol lipid into the diluent formulation was extremely difficult and required approximately 3 days for complete dispersion/dissolution. Thus, the t-butanol blend was not pharmaceutically efficient from a manufacturing perspective.

Example 5

Comparison of Lipid Blends Formulated by Dispersion and Lyophilization in 1) Ethanol:Cyclohexane and 2) an Aqueous Solvent Samples as described in Example 4 were prepared as 1) a ethanol:cyclohexane lipid blend and 2) an aqueous blend. Products were shaken to generate microspheres followed by analysis of number weighted mean sizing on a Particle Sizing Systems (PSS, Santa Barbara, Calif.) Model 770 light obscuration particle sizer, by total particle count, and by determination of % microspheres below 10 μm. The analysis of microspheres below 10 μm is important because of flow of microspheres through the pulmonary capillary bed is limited by the size of the capillaries. No filtration step was incorporated into this demonstration. The aqueous blend resulted in smaller sizes, a greater total number of microspheres, and the % of all microspheres below μm was substantially greater. The results of this study find the aqueous lipid blend to be more efficacious due to more microspheres, safer due to less microspheres greater than 10 μm, and particularly devoid of solid lipid.

Example 6

Comparison of Lipid Blends Formulated by Dispersion and Lyophilization in 1) Ethanol:Cyclohexane and 2) an Aqueous Solvent Samples as described in Example 4, 82%:8%:10%, mole %:mole %:mole % (54%:40%:6% (w:w:w)), of dipalmitoylphosphatidylcholine (DPPC), dipalmitoylphosphatidylethanol-polyethylene glycol 5000 (DPPE-PEG 5000), and dipalmitoylphosphatidic acid (DPPA)) were prepared by 1) the ethanol:cyclohexane lipid blend and 2) the aqueous blend at Ben Venue Laboratories, Bedford, Ohio. Samples, prior to production of a sterile-filled product, were sterile filtered through a Gelman Suporflow 0.2 μm filter (Gelman Scientific, Boston, Mass.). Samples were then sealed in glass vials and the headspace filled with perfluoropropane as described in Example 4.

All HPLC analyses were conducted on a Perkin Elmer Series 200 Quaternary HPLC pump (Perkin Elmer Corp., Norwalk, Conn.) with a Rheodyne Model 9125 Sample Injector, 20 μL sample loop, and Model 7040 4-Way solvent switcher. Evaporative light scattering detection was conducted on an ACS Model 950/14 Mass Detector (Polymer Labs, Inc., Amherst, Mass.) pre-equilibrated to 90° C. All data was transferred to a 80486 DOS compatible PC computer equipped with Perkin Elmer Turbochrome® 4.1 Data Collection and Analysis Software.

HPLC separations were performed with an ASTEC 5 μm spherical diol-bonded 250×4.6 mm steel analytical column (Advanced Separation Technologies, Inc., Whippany, N.J.). The mobile phase for development consisted of a chloroform:methanol:30% aqueous ammonia mixture (90:9:1.0, v:v:v) and an enrichment phase consisting of chloroform:methanol:water:30% aqueous ammonia mixture (60:34:4.0:2.0, v:v:v:v). A profile of the non-linear gradient is provided in FIG. 1 and Table 2. Table 2 provides the peak # (number), the component name, the time in minutes the analyte took to elute from the column, the area under each peak in microvolt (seconds); the height of each peak in microvolt; the area percent of each peak as a percent of the total area of the peaks combined; and the area/heigh in seconds. Note that FIG. 1 sets forth the height (microvolt (seconds) in Table 2) as a response in millivolts.

TABLE 2

| Peak # | Component Name | Time [min] | Area [μV·s] | Height [μV] | Area [%] | Area/Height[s] |
|---|---|---|---|---|---|---|
| 1 | PEG-5000 | 1.838 | 4069080.93 | 371856.56 | 41.70 | 10.94 |
| 2 | DPPC | 11.517 | 5019437.86 | 642372.12 | 51.44 | 7.81 |
| 3 | DPPA | 12.848 | 670139.75 | 94050.55 | 6.87 | 7.13 |
| | | | 9758658.55 | $1.11 \times 10^6$ | 100.00 | |

Solid phase extraction cartridges were first prepped by passing 4.0 ml of methanol through the column. Second, 3.0 ml of HPLC grade water was passed through the cartridge followed by 3.0 ml of the sample preparation. A three ml aliquot containing a lipid mixture with a total lipid concentration of 1 mg ml$^{-1}$ was then loaded onto the cartridge column. The column was then eluted with 6.0 ml of HPLC grade water and the combined eluents discarded. The lipid mixture was then eluted from the column with the following eluents; 1) 10.0 ml of methanol, 2) 10.0 ml of methanol:chloroform (1:1, v:v), and 3) 20 ml of methanol chloroform:water (10:10:3, v:v:v). The three eluents were combined and concentrated in vacuo. The remaining, primarily aqueous residue was then lyophilized by freezing over a dry ice bath and drying until a white powder composed of extracted lipid residue remained. The dry residue was then dissolved in 1 ml of dry chloroform and 20 μl injected onto the HPLC for analysis.

Figure 2A:
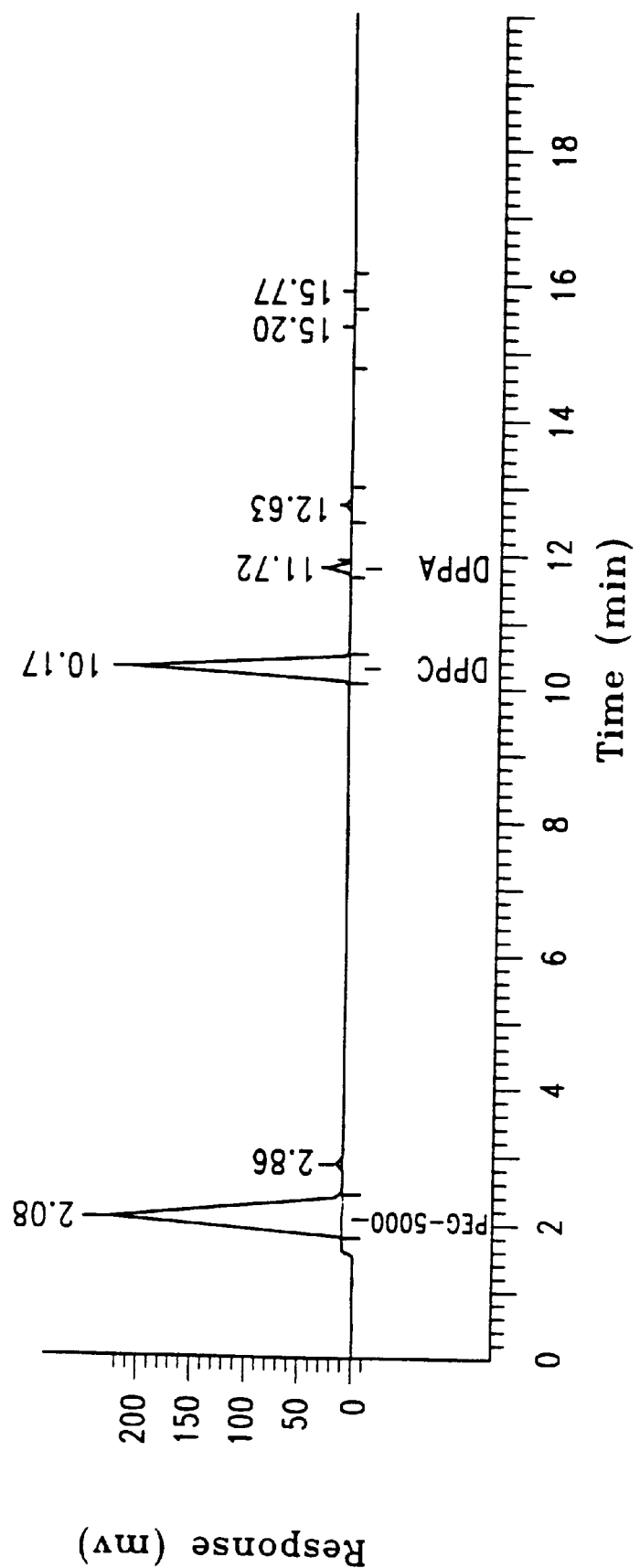
FIG. 2A is an HPLC profile of the lipid blend dispersed and lyophilized from the ethanol:cyclohexane mixture of Example 6.

FIG. 2A is an HPLC profile of the lipid blend dispersed and lyophilized from the ethanol:cyclohexane mixture. Table 3 provides the details of FIG. 2A: the peak # (number), the component name, the time in minutes the analyte took to elute from the column, the area under each peak in microvolt (seconds); the height of each peak in microvolt; the area percent of each peak as a percent of the total area of the peaks combined; and the area/heigh in seconds. Note that FIG. 2A sets forth the height (microvolt (seconds) in Table 3) as a response in millivolts.

TABLE 3

| Peak # | Component Name | Time [min] | Area [μV · s] | Height [μV] | Area [%] | Area/Height[s] |
|---|---|---|---|---|---|---|
| 1 | PEG-5000 | 2.076 | 2563787.96 | 220008.85 | 58.80 | 11.65 |
| 2 | DPPC | 10.170 | 1718951.23 | 208477.65 | 39.43 | 8.25 |
| 4 | DPPA | 11.722 | 77134.40 | 14654.25 | 1.77 | 5.26 |
|  |  |  | 4359873.59 | 443140.75 | 100.00 |  |

Figure 2B:
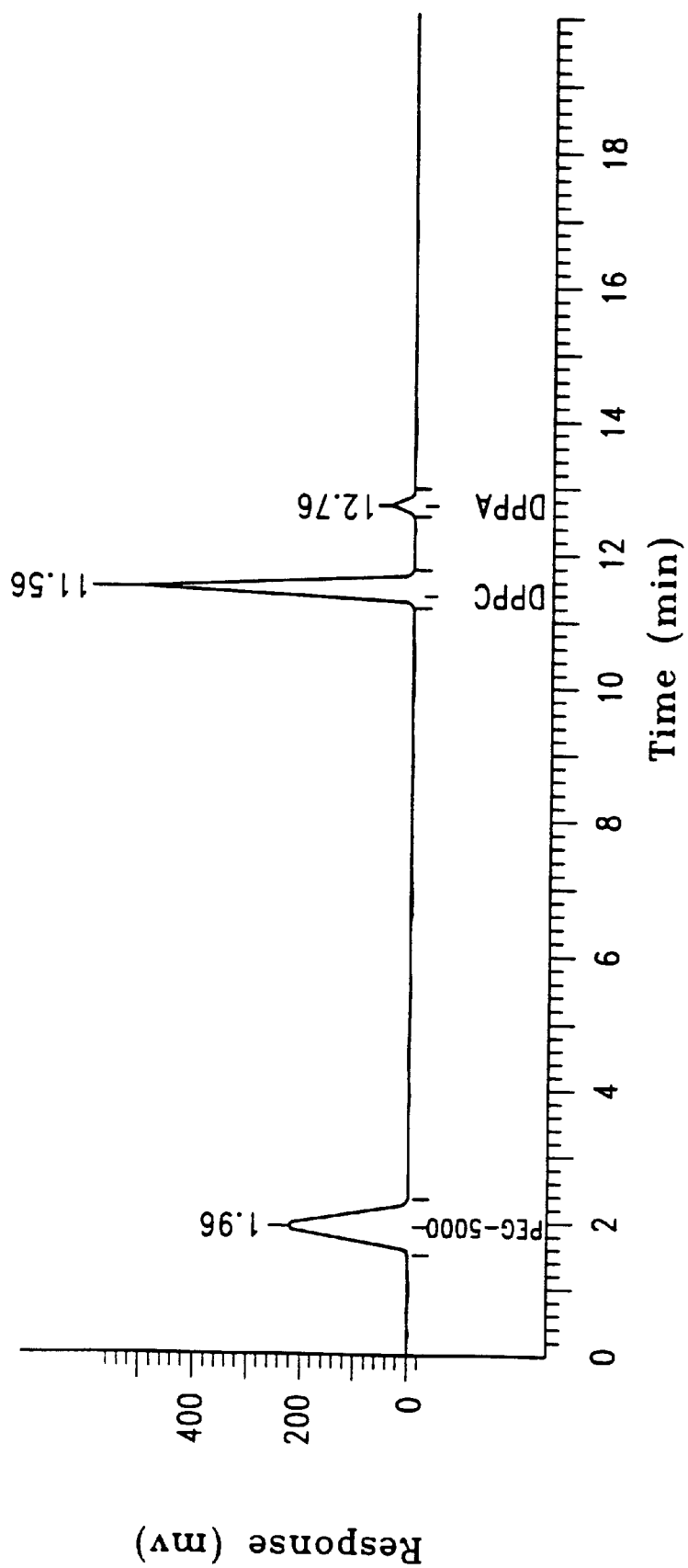
FIG. 2B is an HPLC profile of the lipid blend dispersed and lyophilized from the aqueous blend of Example 6.

FIG. 2B is an HPLC profile of the lipid blend dispersed and lyophilized from the aqueous blend. Table 4 provides the details of FIG. 2B: the peak # (number), component name, time in minutes the analyte took to elute from the column, area under each peak in microvolt (seconds); the height of each peak in microvolt; the area percent of each peak as a percent of the total area of the peaks combined; and the area/heigh in seconds. Note that FIG. 2B sets forth the height (microvolt (seconds) in Table 4) as a response in millivolts.

TABLE 4

| Peak # | Component Name | Time [min] | Area [μV · s] | Height [μV] | Area [%] | Area/Height[s] |
|---|---|---|---|---|---|---|
| 1 | PEG-5000 | 1.956 | 3733461.39 | 215714.27 | 42.73 | 17.31 |
| 2 | DPPC | 11.558 | 4523259.40 | 555075.04 | 51.77 | 8.15 |
| 3 | DPPA | 12.756 | 481181.83 | 67502.11 | 5.51 | 7.13 |
|  |  |  | 8737902.62 | 838291.42 | 100.00 |  |

The quantitation of the extraction from the aqueous blend is indicative of the starting lipid proportions originally prepared. In particular, the negatively charged lipid, phosphatidic acid, in the aqueous blend is dispersed and dissolved more efficiently with less incidental losses due to filtration than the organic solvent blend. This demonstrates that the aqueous blend is pharmaceutically easier to analyze and that losses by filtration do not significantly alter the indicated proportions of lipids.

Example 7

Demonstration of Superior Ultrasonic Imaging Capabilities Using Aqueous Blended Lipid vs. Cyclohexane-Ethanol Blended Lipid Phase I human clinical trials conducted with a Good Manufacturing Practice (GMP) produced batch of cyclohexane:ethanol blended lipid (GMP-1), and an aqueous blended lipid (GMP-2). Microspheres prepared as described in Example 4 were administered to healthy adult males during a Phase I Clinical trial. Comparative doses of 5 μL/kg, 10 μL/kg, and 15 μL/kg were administered intravenously in the forearm. Ultrasonic imaging was performed on the heart region with 2.5 Mhz, 3.5 Mhz, and 5 Mhz transducers. Imaging demonstrated particular acuity in opacification of the myocardial (muscle tissue) region of the heart when the GMP-2 formulation was used compared to the GMP-1 formulation. This demonstrates the superiority of the blend. The aqueous blend results in ease of preparation for manufacturing, more efficient manufacturing, and superior imaging capabilities.

The disclosures of each patent, patent application and publication cited or described in this document are hereby incorporated herein by reference, in their entirety.

Various modifications of the invention, in addition to those described herein, will be apparent to those skilled in the art from the foregoing description. Such modifications are also intended to fall within the scope of the appended claims.

What is claimed is:

1. A method for preparing a fluorine-containing gas-filled microsphere comprising:
   a. reconstituting the lipids dipalmitoylphosphatidylcholine, dipalmitoylphosphatidylethanolaminepolyethylene glycol, and dipalmitoylphosphatidic acid in a ratio of about 70 to about 90 mole %, about 5 to about 15 mole %, and about 5 to about 15 mole %, respectively, in an aqueous solution to a concentration of about 20 mg/ml to about 50 mg/ml to form a lipid-containing aqueous solution;
   b. lyophilizing said lipid-containing aqueous solution to form a lyophilized composition such that the dipalmitoylphosphatidylcholine, dipalmitoylphosphatidylethanolamine-polyethylene glycol, and dipalmitoylphosphatidic acid ratio of about 70 to about 90 mole %, about 5 to about 15 mole %, and about 5 to about 15 mole %, respectively, is uniform throughout the composition;

c. dispersing said lyophilized composition in an aqueous-based pharmaceutically acceptable carrier to a concentration of about 0.1 mg/ml to about 5 mg/ml to form an aqueous microsphere-forming solution;

d. introducing a fluorine-containing gas into said aqueous microsphere-forming solution; and e. shaking said aqueous microsphere-forming solution to form a microsphere filled with fluorine-containing gas.

2. The method of claim 1 wherein the shaking step comprises vortexing.

3. The method of claim 1 further comprising the steps of filtering said aqueous microsphere-forming solution.

4. The method of claim 1 further comprising extruding the aqueous microsphere-forming solution through at least one filter of a selected pore size.

5. The method of claim 4 wherein the pore size is about 10 μm or smaller.

6. The method as in claim 4 wherein the pore size is about 0.22 μm.

7. The method of claim 1 further comprising heating said aqueous microsphere-forming solution.

8. The method of claim 4 further comprising dispersing said aqueous microsphere-forming solution into at least one vessel.

9. The method of claim 1 wherein step d. comprises placing a vessel containing said aqueous microsphere-forming solution in a chamber and introducing a fluorine-containing gas into said chamber, and step e. comprises shaking said vessel to form a microsphere filled with flourine-containing gas.

10. The method of claim 9 further comprising pressurizing said vessel.

11. The method of claim 1 wherein step d. comprises placing a vessel containing said aqueous microsphere-forming solution in a pressurized chamber, evacuating the chamber of gas, and filling the chamber with a fluorine-containing gas such that the head space of the vessel is filled with a fluorine-containing gas and step e. comprises shaking said vessel to form a microsphere filled with a fluorine-containing gas.

12. The method of claim 1 wherein said aqueous solution is selected from the group consisting of water, physiological saline, and normal saline.

13. The method of claim 1 wherein said pharmaceutically acceptable carrier is selected from the group consisting of a mixture of water, glycerol, and propylene glycol and a mixture of saline, glycerol, and propylene glycol in a ratio of 8:1:1, v:v:v, respectively.

14. The method of claim 1 wherein step d. comprises placing a vessel containing said aqueous microsphere-forming solution in a chamber and introducing a perfluorocarbon, and step e. comprises shaking said vessel to form a perfluorocarbon-containing microsphere.

15. The method of claim 14 wherein step d. comprises placing a vessel containing said aqueous microsphere-forming solution in a chamber and introducing a perfluorocarbon selected from the group consisting of perfluoropropane and perfluorobutane into said chamber, and step e. comprises shaking said vessel to form a perfluorocarbon-containing microsphere.

16. The method of claim 1 wherein step d. comprises placing a vessel containing said aqueous microsphere-forming solution in a pressurized chamber, evacuating the chamber of gas, and filing the chamber with a perfluorocarbon such that the head space of the vessel is filled with a perfluorocarbon, and step e. comprises shaking said vessel to form a perfluorocarbon-containing microsphere.

17. The method of claim 16 wherein step d. comprises placing a vessel containing said aqueous microsphere-forming solution in a pressurized chamber, evacuating the chamber of gas, and filing the chamber with a perfluorocarbon selected from the group consisting of perfluoropropane and perfluorobutane such that the head space of the vessel is filled with a perfluorocarbon, and step e. comprises shaking said vessel to form a perfluorocarbon-containing microsphere.

18. The method of claim 1 wherein said fluorine-containing gas is selected from the group consisting of sulfur hexafluoride and a perfluorocarbon.

19. The method of claim 18 wherein said perfluorocarbon gas is selected from the group consisting of perfluoropropane, perfluoropentane, perfluorohexane, and perfluorobutane.

20. A method of claim 1 wherein said lipids comprise a monolayer.

21. A method of claim 20 wherein said gas is selected from the group consisting of sulfur hexafluoride and a perfluorocarbon.

22. A method of claim 21 wherein said perfluorocarbon is selected from the group consisting of perfluorobutane, perfluoropropane, perfluoropentane, and perfluorohexane.

* * * * *

UNITED STATES PATENT AND TRADEMARK OFFICE
CERTIFICATE OF CORRECTION

PATENT NO.    : 6,033,646
DATED         : March 7, 2000
INVENTOR(S)   : Evan C. Unger et al.

It is certified that error appears in the above-identified patent and that said Letters Patent is hereby corrected as shown below:

Title page, Item [54] and Column 1, line 1,
Please delete the title "METHOD OF PREPARING FLUORINATED GAS MICROSPHERES" and insert -- NOVEL DISPERSIBLE LIPID BLEND AND USES THEREFOR -- therefor.

Title page,
Item [56], References Cited, U.S. PATENT DOCUMENTS, please add
-- 5,620,689  4/1997  Allen et al.  424/178.1 --.
FOREIGN PATENT DOCUMENTS, please delete
"WO 84/02909  8/1994  WIPO" and insert -- WO 94/02909  8/1994  WIPO -- therefor.
OTHER PUBLICATIONS, "Sigel, H.," reference, please delete "*Antiobiotics*" and insert -- *Antibiotics* -- therefor.
"Shiina et al.," reference, please delete "Hyperthermiably" and insert -- Hyperthermia by -- therefor.
"Hug et al.," reference, please delete "*Biochmimica*" and insert -- *Biochimica* -- therefor.
"Ter-Pogossian," reference, please delete "*Tomography*, Kee, et al., n." and insert -- *Computed Body Tomography*, Lee, et al., eds., -- therefor.
"Ter-Pogossian," reference, please delete "*Computed Body eds.,*".
"Aronberg," reference, please delete "Kee" and insert -- Lee -- therefor.
"Dittrich," reference, please insert -- abstract -- after "(May 7, 1996)".
"Pantely," reference, please insert -- abstract -- after "(May 7, 1996)".
"Ophir et al.," reference, please delete "*Ultrasonic*" and insert -- *Ultrasound* -- therefor.
"Encyclopedia of...," reference, please delete "Acience" and insert -- Science -- therefor.
"Villanueva et al.," reference, please delete "Patters" and insert -- Patterns -- therefor.

Column 12,
Line 12, please delete "one years" and insert -- one year -- therefor.

Column 18,
Line 54, please delete "area/heigh" and insert -- area/height -- therefor.

Column 19,
Lines 26 and 47, please delete "area/heigh" and insert -- area/height -- therefor.

UNITED STATES PATENT AND TRADEMARK OFFICE
CERTIFICATE OF CORRECTION

PATENT NO.   : 6,033,646
DATED        : March 7, 2000
INVENTOR(S)  : Evan C. Unger et al.

It is certified that error appears in the above-identified patent and that said Letters Patent is hereby corrected as shown below:

Column 22,
Lines 20 and 27, please delete "filing" and insert -- filling -- therefor.

Signed and Sealed this

Twenty-first Day of December, 2004

JON W. DUDAS
*Director of the United States Patent and Trademark Office*